US010752745B2

(12) United States Patent
Topolkaraev et al.

(10) Patent No.: US 10,752,745 B2
(45) Date of Patent: *Aug. 25, 2020

(54) POLYOLEFIN FILM FOR USE IN PACKAGING

(71) Applicant: Kimberly-Clark Worldwide, Inc., Neenah, WI (US)

(72) Inventors: Vasily A. Topolkaraev, Appleton, WI (US); Ryan J. McEneany, Appleton, WI (US); Mark M. Mleziva, Appleton, WI (US); Brent M. Thompson, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/895,231

(22) PCT Filed: Jun. 6, 2014

(86) PCT No.: PCT/IB2014/062020
§ 371 (c)(1),
(2) Date: Dec. 2, 2015

(87) PCT Pub. No.: WO2014/199271
PCT Pub. Date: Dec. 18, 2014

(65) Prior Publication Data
US 2016/0122484 A1  May 5, 2016

Related U.S. Application Data

(60) Provisional application No. 61/833,980, filed on Jun. 12, 2013, provisional application No. 61/907,572, filed on Nov. 22, 2013.

(51) Int. Cl.
*C08J 9/00* (2006.01)
*C08J 5/18* (2006.01)
(Continued)

(52) U.S. Cl.
CPC ............. *C08J 9/0061* (2013.01); *A61F 13/53* (2013.01); *A61L 15/225* (2013.01); *A61L 15/24* (2013.01);
(Continued)

(58) Field of Classification Search
CPC ...... C08J 5/18; C08J 2323/12; C08J 2467/04; C08J 2423/08
See application file for complete search history.

(56) References Cited

U.S. PATENT DOCUMENTS 3,354,506 A  11/1967  Raley
3,423,255 A  1/1969  Joyce
(Continued)

FOREIGN PATENT DOCUMENTS

CN  1247545  3/2000
EP  0348887 A2  1/1990
(Continued)

OTHER PUBLICATIONS

Translation of JP 2008 144039, Kondo et al., Jun. 26, 2008, p. 1-34. (Year: 2008).*
(Continued)

*Primary Examiner* — Hai Vo
(74) *Attorney, Agent, or Firm* — Dority & Manning, P.A.

(57) ABSTRACT

A polyolefin packaging film is provided. The polyolefin film is formed by a thermoplastic composition containing a continuous phase that includes a polyolefin matrix polymer and nanoinclusion additive is provided. The nanoinclusion additive is dispersed within the continuous phase as discrete nano-scale phase domains. When drawn, the nano-scale phase domains are able to interact with the matrix in a unique manner to create a network of nanopores.

26 Claims, 3 Drawing Sheets

(51) Int. Cl.
*C08L 23/02* (2006.01)
*B01D 71/26* (2006.01)
*D01F 1/10* (2006.01)
*D01F 1/08* (2006.01)
*D01F 6/06* (2006.01)
*B01D 67/00* (2006.01)
*D01D 5/247* (2006.01)
*C08L 67/00* (2006.01)
*C08L 23/08* (2006.01)
*D01F 6/46* (2006.01)
*A61F 13/53* (2006.01)
*A61L 15/22* (2006.01)
*A61L 15/24* (2006.01)
*A61L 15/42* (2006.01)
*B29C 55/00* (2006.01)
*B32B 3/26* (2006.01)
*B32B 5/02* (2006.01)
*B32B 27/32* (2006.01)
*C08J 9/28* (2006.01)
*B29C 55/14* (2006.01)
*B29C 55/20* (2006.01)
*B32B 27/20* (2006.01)
*C08L 23/12* (2006.01)
*B29K 105/16* (2006.01)
*B29K 23/00* (2006.01)
*B29K 105/04* (2006.01)
*B29K 63/00* (2006.01)
*B29L 7/00* (2006.01)

(52) U.S. Cl.
CPC ........ *A61L 15/425* (2013.01); *B01D 67/0027* (2013.01); *B01D 71/26* (2013.01); *B29C 55/005* (2013.01); *B29C 55/14* (2013.01); *B29C 55/20* (2013.01); *B32B 3/26* (2013.01); *B32B 5/022* (2013.01); *B32B 27/205* (2013.01); *B32B 27/32* (2013.01); *C08J 5/18* (2013.01); *C08J 9/0023* (2013.01); *C08J 9/0095* (2013.01); *C08J 9/28* (2013.01); *C08L 23/02* (2013.01); *C08L 23/0815* (2013.01); *C08L 23/0884* (2013.01); *C08L 23/12* (2013.01); *C08L 67/00* (2013.01); *D01D 5/247* (2013.01); *D01F 1/08* (2013.01); *D01F 1/10* (2013.01); *D01F 6/06* (2013.01); *D01F 6/46* (2013.01); *B29K 2023/00* (2013.01); *B29K 2023/12* (2013.01); *B29K 2063/00* (2013.01); *B29K 2105/041* (2013.01); *B29K 2105/162* (2013.01); *B29L 2007/007* (2013.01); *B32B 2264/0235* (2013.01); *B32B 2264/0278* (2013.01); *B32B 2307/726* (2013.01); *B32B 2307/7265* (2013.01); *B32B 2432/00* (2013.01); *B32B 2439/70* (2013.01); *B32B 2555/02* (2013.01); *C08J 2201/02* (2013.01); *C08J 2201/0522* (2013.01); *C08J 2205/042* (2013.01); *C08J 2323/06* (2013.01); *C08J 2323/08* (2013.01); *C08J 2323/12* (2013.01); *C08J 2423/08* (2013.01); *C08J 2433/10* (2013.01); *C08J 2433/14* (2013.01); *C08J 2467/04* (2013.01); *C08L 2205/03* (2013.01)

(56) References Cited

U.S. PATENT DOCUMENTS

| | | |
|---|---|---|
| 3,650,649 A | 3/1972 | Schippers |
| 3,801,429 A | 4/1974 | Schrenk et al. |
| 3,802,817 A | 4/1974 | Matsuki et al. |
| 3,855,046 A | 12/1974 | Hansen et al. |
| 4,041,203 A | 8/1977 | Brock et al. |
| 4,100,324 A | 7/1978 | Anderson et al. |
| 4,282,735 A | 8/1981 | Break |
| 4,374,888 A | 2/1983 | Bornslaeger |
| 4,557,132 A | 12/1985 | Break |
| 4,698,372 A | 10/1987 | Moss |
| 4,704,116 A | 11/1987 | Enloe |
| 4,766,029 A | 8/1988 | Brock et al. |
| 4,797,468 A | 1/1989 | De Vries |
| 4,798,603 A | 1/1989 | Meyer et al. |
| 4,801,494 A | 1/1989 | Datta et al. |
| 4,908,026 A | 3/1990 | Sukiennik et al. |
| 4,937,299 A | 6/1990 | Ewen et al. |
| D315,990 S | 4/1991 | Blenke et al. |
| 5,169,706 A | 12/1992 | Collier, IV et al. |
| 5,179,164 A | 1/1993 | Lausberg et al. |
| 5,192,606 A | 3/1993 | Proxmire et al. |
| 5,213,881 A | 5/1993 | Timmons et al. |
| 5,218,071 A | 6/1993 | Tsutsui et al. |
| 5,248,309 A | 9/1993 | Serbiak et al. |
| 5,272,236 A | 12/1993 | Lai et al. |
| 5,278,272 A | 1/1994 | Lai et al. |
| 5,284,309 A | 2/1994 | Salvatore et al. |
| 5,284,703 A | 2/1994 | Everhart et al. |
| 5,322,728 A | 6/1994 | Davey et al. |
| 5,350,624 A | 9/1994 | Georger et al. |
| D358,035 S | 5/1995 | Zander et al. |
| 5,464,688 A | 11/1995 | Timmons et al. |
| 5,470,944 A | 11/1995 | Bonsignore |
| 5,472,775 A | 12/1995 | Obijeski et al. |
| 5,486,166 A | 1/1996 | Bishop et al. |
| 5,490,846 A | 2/1996 | Ellis et al. |
| 5,539,056 A | 7/1996 | Yang et al. |
| 5,571,619 A | 11/1996 | McAlpin et al. |
| 5,596,052 A | 1/1997 | Resconi et al. |
| 5,620,779 A | 4/1997 | Levy et al. |
| D384,508 S | 10/1997 | Zander et al. |
| D384,819 S | 10/1997 | Zander et al. |
| 5,702,377 A | 12/1997 | Collier, IV et al. |
| D390,708 S | 2/1998 | Brown |
| 5,766,760 A | 6/1998 | Tsai et al. |
| 5,770,682 A | 6/1998 | Ohara et al. |
| 5,821,327 A | 10/1998 | Oota et al. |
| 5,843,057 A | 12/1998 | McCormack |
| 5,855,999 A | 1/1999 | McCormack |
| 5,880,254 A | 3/1999 | Ohara et al. |
| 5,931,823 A | 8/1999 | Stokes et al. |
| 5,932,497 A | 8/1999 | Morman et al. |
| 5,962,112 A | 10/1999 | Haynes et al. |
| 5,968,643 A | 10/1999 | Topolkaraev et al. |
| 5,997,981 A | 12/1999 | McCormack et al. |
| 6,002,064 A | 12/1999 | Kobylivker et al. |
| D418,305 S | 1/2000 | Zander et al. |
| 6,015,764 A | 1/2000 | McCormack et al. |
| 6,037,033 A | 3/2000 | Hunter |
| 6,037,281 A | 3/2000 | Mathis et al. |
| 6,060,638 A | 5/2000 | Paul et al. |
| 6,071,451 A | 6/2000 | Wang et al. |
| D428,267 S | 7/2000 | Romano, III et al. |
| 6,090,325 A | 7/2000 | Wheat et al. |
| 6,093,665 A | 7/2000 | Sayovitz et al. |
| 6,096,014 A | 8/2000 | Haffner et al. |
| 6,111,163 A | 8/2000 | McCormack et al. |
| 6,150,002 A | 11/2000 | Varona |
| 6,214,933 B1 | 4/2001 | Wang et al. |
| 6,268,048 B1 | 7/2001 | Topolkaraev et al. |
| 6,326,458 B1 | 12/2001 | Gruber et al. |
| 6,380,445 B1 | 4/2002 | Rietz et al. |
| 6,389,864 B1 | 5/2002 | Chubb et al. |
| 6,461,457 B1 | 10/2002 | Taylor et al. |
| 6,485,446 B1 | 11/2002 | Brother et al. |
| 6,500,563 B1 | 12/2002 | Datta et al. |
| 6,582,810 B2 | 6/2003 | Heffelfinger |
| 6,586,073 B2 | 7/2003 | Perez et al. |
| 6,642,429 B1 | 11/2003 | Carter et al. |
| 6,663,611 B2 | 12/2003 | Blaney et al. |
| 6,716,203 B2 | 4/2004 | Sorebo et al. |
| 6,824,680 B2 | 11/2004 | Chandavasu et al. |

(56) References Cited

U.S. PATENT DOCUMENTS

| | | | |
|---|---|---|---|
| 6,824,734 B2 | 11/2004 | Boggs et al. | |
| 7,060,867 B2 | 6/2006 | Jameson | |
| 7,097,904 B2 | 8/2006 | Ochi et al. | |
| 7,141,168 B2 | 11/2006 | Sakamoto et al. | |
| 7,341,776 B1 | 3/2008 | Milliren et al. | |
| 7,984,591 B2 | 7/2011 | Cashin et al. | |
| 7,998,579 B2 | 8/2011 | Lin et al. | |
| 8,105,682 B2 | 1/2012 | Sun et al. | |
| 8,268,738 B2 | 9/2012 | McEneany et al. | |
| 8,313,818 B2 | 11/2012 | Vo et al. | |
| 8,323,837 B2 | 12/2012 | Nishida et al. | |
| 8,334,327 B2 | 12/2012 | Kaufman et al. | |
| 8,362,145 B2 | 1/2013 | Li et al. | |
| 8,603,614 B2 | 12/2013 | Lam et al. | |
| 8,759,446 B2 | 6/2014 | Li et al. | |
| 8,936,740 B2 | 1/2015 | Topolkaraev et al. | |
| 9,127,915 B1* | 9/2015 | Tsai | B32B 27/12 |
| 10,240,260 B2* | 3/2019 | Topolkaraev | B29C 48/0012 |
| 10,286,593 B2* | 5/2019 | Topolkaraev | C08J 9/0061 |
| 10,640,898 B2* | 5/2020 | Topolkaraev | B01J 20/265 |
| 2003/0116462 A1 | 6/2003 | Sorebo et al. | |
| 2004/0002273 A1 | 1/2004 | Fitting et al. | |
| 2005/0054255 A1 | 3/2005 | Morman et al. | |
| 2005/0059941 A1 | 3/2005 | Baldwin et al. | |
| 2005/0245162 A1 | 11/2005 | McCormack et al. | |
| 2009/0318884 A1 | 12/2009 | Meyer et al. | |
| 2009/0326152 A1* | 12/2009 | Li | C08L 23/10 525/190 |
| 2010/0305529 A1 | 12/2010 | Ashton et al. | |
| 2010/0313507 A1 | 12/2010 | Castro et al. | |
| 2011/0091714 A1 | 4/2011 | Chen et al. | |
| 2011/0183563 A1 | 7/2011 | Ochi et al. | |
| 2011/0252739 A1 | 10/2011 | Leeser et al. | |
| 2011/0256346 A1 | 10/2011 | Bowden et al. | |
| 2011/0256364 A1 | 10/2011 | Boyer et al. | |
| 2012/0040185 A1 | 2/2012 | Topolkaraev et al. | |
| 2012/0109090 A1 | 5/2012 | Reichardt et al. | |
| 2012/0202905 A1* | 8/2012 | Busch | B01D 67/0027 521/143 |
| 2012/0225272 A1 | 9/2012 | Costeux et al. | |
| 2012/0231242 A1 | 9/2012 | Boyer et al. | |
| 2013/0017430 A1* | 1/2013 | Terakawa | B32B 27/32 429/144 |
| 2014/0011015 A1* | 1/2014 | Gardner | B29C 67/202 428/315.5 |
| 2016/0102185 A1* | 4/2016 | Topolkaraev | C08J 3/203 521/134 |
| 2016/0108194 A1* | 4/2016 | Topolkaraev | C08L 67/04 428/76 |
| 2016/0114071 A1* | 4/2016 | Topolkaraev | B01D 67/0027 604/370 |
| 2016/0115291 A1* | 4/2016 | Topolkaraev | B01D 67/0027 442/370 |
| 2016/0120247 A1* | 5/2016 | Topolkaraev | A41B 17/00 442/184 |
| 2016/0122491 A1* | 5/2016 | Topolkaraev | C08K 9/04 521/135 |
| 2016/0130799 A1* | 5/2016 | Topolkaraev | E04B 1/74 52/408 |

FOREIGN PATENT DOCUMENTS

| | | |
|---|---|---|
| EP | 0348887 A3 | 1/1990 |
| EP | 0609881 A1 | 8/1994 |
| EP | 0609881 B1 | 8/1999 |
| EP | 1152025 A1 | 11/2001 |
| EP | 1152025 A4 | 11/2001 |
| EP | 1955845 | 8/2008 |
| EP | 2233524 | 9/2010 |
| EP | 2543697 | 1/2013 |
| JP | 2008144039 A * | 6/2008 |
| JP | 2011074214 | 4/2011 |
| JP | 2011526949 | 10/2011 |
| JP | 2013100487 | 5/2013 |
| JP | 2014061505 | 4/2014 |
| WO | WO 99/32272 A1 | 7/1999 |
| WO | WO2009/152021 A2 | 12/2009 |
| WO | WO2009/152021 A3 | 12/2009 |
| WO | WO2008026684 | 1/2010 |
| WO | WO 2013118021 | 8/2013 |
| WO | WO2014/199268 | 12/2014 |
| WO | WO2014/199269 | 12/2014 |
| WO | WO2014/199270 | 12/2014 |
| WO | WO2014/199272 | 12/2014 |
| WO | WO2014/199273 | 12/2014 |
| WO | WO2014/199274 | 12/2014 |
| WO | WO2014/199275 | 12/2014 |
| WO | WO2014/199276 | 12/2014 |
| WO | WO2014/199277 | 12/2014 |
| WO | WO2014/199278 | 12/2014 |
| WO | WO2014/199279 | 12/2014 |

OTHER PUBLICATIONS

Lee et al., "Development of Discrete Nanopores I: Tension of Polypropylene/Polyethylene Copolymer Blends," *Journal of Applied Polymer Science*, vol. 91, No. 6, Mar. 15, 2004, pp. 3462-3650.

International Search Report and Written Opinion for PCT/IB2014/062020 dated Sep. 24, 2014, 12 pages.

Supplementary European Search Report for EP 14811253 dated Nov. 23, 2016, 7 pages.

* cited by examiner

POLYOLEFIN FILM FOR USE IN PACKAGING

RELATED APPLICATIONS

The present application is the national stage entry of International Patent Application No. PCT/IB2014/062020 having a filing date of Jun. 6, 2014, which claims priority to U.S. Provisional Application Ser. Nos. 61/833,980 (filed on Jun. 12, 2013) and 61/907,572 (filed on Nov. 22, 2013), which are incorporated herein by reference.

BACKGROUND OF THE INVENTION

Packaging films are often formed from polyolefin materials, such as linear low density polyethylene ("LLDPE"), low density polyethylene ("LDPE"), or high density polyethylene ("HDPE"). In recent years, however, petroleum resources have become more expensive and manufacturers and consumers alike have become more aware of the sustainability need for films with a smaller carbon footprint, which means reduced carbon emissions during the entire product life cycle. While attempts have been made to add various additives to reduce the content of petroleum-derived olefinic polymers, this usually results in a corresponding decrease in some mechanical properties (e.g., ductility) or tensile strength, etc.) of the film, which is highly undesirable. As such, a need currently exists for packaging films that can have a reduced consumption of petroleum-based polymers, but yet can also exhibit good properties.

SUMMARY OF THE INVENTION

In accordance with one embodiment of the present invention, a film is disclosed that comprises a thermoplastic composition. The composition contains a continuous phase that includes a polyolefin matrix polymer and a nanoinclusion additive dispersed within the continuous phase in the form of discrete domains. A porous network is defined in the composition that includes a plurality of nanopores having an average cross-sectional dimension of about 800 nanometers or less.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

DETAILED DESCRIPTION OF REPRESENTATIVE EMBODIMENTS

Figure 1:
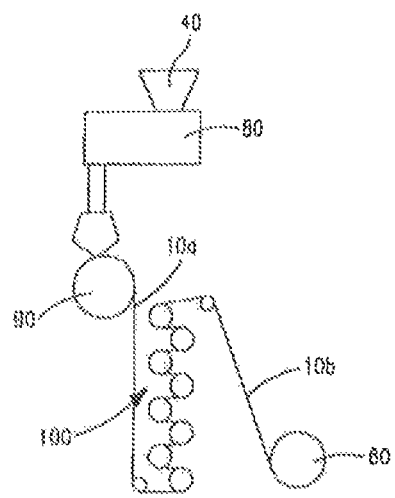
FIG. 1 is a schematic illustration of one embodiment of a method for forming the film of the present invention.

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a packaging film that contains a thermoplastic composition. The thermoplastic composition contains a continuous phase that includes a polyolefin matrix polymer, and also contains a nanoinclusion additive that is at least partially incompatible with the polyolefin matrix polymer so that it becomes dispersed within the continuous phase as discrete nano-scale phase domains. During drawing, when the composition is subjected to a deformation and elongational strain, the present inventors have discovered that these nano-scale phase domains are able to interact in a unique manner to create network of pores. Namely, it is believed that elongational strain can initiate intensive localized shear zones and/or stress intensity zones (e.g., normal stresses) near the discrete phase domains as a result of stress concentrations that arise from the incompatibility of the materials. These shear and/or stress intensity zones cause some initial debonding in the polyolefin matrix adjacent to the domains. Once initial pores are formed, the matrix located between domains can deform plastically to create internal stretched areas that locally narrow (or neck) and strain-harden. This process allows the formation of pores through the bulk of the composition that grow in the stretching direction, thereby leading to the formation of a porous network while the molecular orientation leads to strain-hardening that enhances mechanical strength.

Through the techniques noted above, a unique porous network may be formed in the polyolefin film so that the average percent volume occupied by the pores within a given unit volume of the material may be from about 15% to about 80% per $cm^3$, in some embodiments from about 20% to about 70%, and in some embodiments, from about 30% to about 60% per cubic centimeter of the material. With such a pore volume, the composition may have a relatively low density, such as about 0.90 grams per cubic centimeter ("$g/cm^3$") or less, in some embodiments about 0.85 $g/cm^3$ or less, in some embodiments about 0.80 $g/cm^3$ or less in some embodiments from about 0.10 $g/cm^3$ to about 0.75 $g/cm^3$, and in some embodiments, from about 0.20 $g/cm^3$ to about 0.70 $g/cm^3$. A substantial portion of pores in the porous network are also of a "nano-scale" size ("nanopores"), such as those having an average cross-sectional dimension of about 800 nanometers or less, in some embodiments from about 5 to about 700 nanometers, and in some embodiments, from about 10 to about 500 nanometers. The term "cross-sectional dimension" generally refers to a characteristic dimension (e.g., width or diameter) of a pore, which is substantially orthogonal to its major axis (e.g., length) and also typically substantially orthogonal to the direction of the stress applied during drawing. The nanopores may also have an average axial dimension within the range of from about 100 to about 5000 nanometers, in some embodiments from about 50 to about 2000 nanometers, and in some embodiments, from about 100 to about 1000 nanometers. The "axial dimension" is the dimension in the direction of the major axis (e.g. length), which is typically in the direction of drawing. Such nanopores may, for example, constitute about 15 vol. % or more, in some embodiments about 20 vol. % or more, in some embodiments from about 30 vol. % to 100 vol. %, and in some embodiments, from about 40 vol. % to about 90 vol. % of the total pore volume in the polyolefin film.

Besides a reduced density, the nanoporous structure may also provide a variety of additional different benefits to the resulting polyolefin film. For example, such a structure can help restrict the flow of fluids through the film and be generally impermeable to fluids (e.g., liquid water), thereby allowing the film to insulate a surface from water penetration. In this regard, the polyolefin film may have a relatively high hydrohead value of about 50 centimeters ("cm") or more, in some embodiments about 100 cm or more, in some embodiments, about 150 cm or more, and in some embodiments, from about 200 cm to about 1000 cm, as determined in accordance with ATTCC 127-2008. Other beneficial properties may also be achieved. For example, the resulting polyolefin film may be generally permeable to water vapors. The permeability of the film to water vapor may characterized by its relatively high water vapor transmission rate ("WVTR"), which is the rate at which water vapor permeates through a film as measured in units of grams per meter squared per 24 hours ($g/m^2/24$ hr). For example, the polyolefin film may exhibit a WVTR of about 300 $g/m^2$-24 hours or more, in some embodiments about 500 $g/m^2$-24 hours or more, in some embodiments about 1,000 $g/m^2$-24 hours or more, and in some embodiments, from about 3,000 to about 15,000 $g/m^2$-24 hours, such as determined in accordance with ASTM E96/96M-12, Procedure B or INDA Test Procedure IST-70.4 (01).

Various embodiments of the present invention will now be described in more detail.

I. Thermoplastic Composition

A. Polyolefin Matrix

Polyolefins typically constitute from about 60 to about 99 wt. %, in some embodiments from about 60 wt. % to about 98 wt. %, and in some embodiments, from about 80 wt. % to about 95 wt. % of the thermoplastic composition. The polyolefin may have a melting temperature of from about 100° C. to about 220° C., in some embodiments from about 120° C. to about 200° C., and in some embodiments, from about 140° C. to about 180° C. The melting temperature may be determined using differential scanning calorimetry ("DSC") in accordance with ASTM D-3417. Suitable polyolefins may, for instance, include ethylene polymers (e.g., low density polyethylene ("LDPE"), high density polyethylene ("HDPE"), linear low density polyethylene ("LLDPE"), etc.), propylene homopolymers (e.g., syndiotactic, atactic, isotactic, etc.), propylene copolymers, and so forth. In one particular embodiment, the polymer is a propylene polymer, such as homopolypropylene or a copolymer of propylene. The propylene polymer may, for instance, be formed from a substantially isotactic polypropylene homopolymer or a copolymer containing equal to or less than about 10 wt. % of other monomers, i.e., at least about 90% by weight propylene Such homopolymers may have a melting point of from about 140° C. to about 170° C.

Of course, other polyolefins may also be employed in the composition of the present invention. In one embodiment, for example, the polyolefin may be a copolymer of ethylene or propylene with another α-olefin, such as a $C_3$-$C_{20}$ α-olefin or $C_3$-$C_{12}$ α-olefin. Specific examples of suitable α-olefins include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are 1-butene, 1-hexene and 1-octene. The ethylene or propylene content of such copolymers may be from about 60 mole % to about 99 mole %, in some embodiments from about 80 mole % to about 98.5 mole %, and in some embodiments, from about 87 mole % to about 97.5 mole %. The α-olefin content may likewise range from about 1 mole % to about 40 mole %, in some embodiments from about 1.5 mole % to about 15 mole %, and in some embodiments, from about 2.5 mole % to about 13 mole %.

Exemplary olefin copolymers for use in the present invention include ethylene-based copolymers available under the designation EXACT™ from ExxonMobil Chemical Company of Houston, Tex. Other suitable ethylene copolymers are available under the designation ENGAGE™, AFFINITY™, DOWLEX™ (LLDPE) and ATTANE™ (ULDPE) from Dow Chemical Company of Midland, Mich. Other suitable ethylene polymers are described in U.S. Pat. No. 4,937,299 to Ewen et al.; U.S. Pat. No. 5,218,071 to Tsutsui et al.; U.S. Pat. No. 5,272,236 to Lai, et al.; and U.S. Pat. No. 5,278,272 to Lai, et al. Suitable propylene copolymers are also commercially available under the designations VISTAMAXX™ from ExxonMobil Chemical Co. of Houston, Tex.; FINA™ (e.g., 8573) from Atofina Chemicals of Feluy, Belgium; TAFMER™ available from Mitsui Petrochemical Industries; and VERSIFY™ available from Dow Chemical Co. of Midland, Mich. Suitable polypropylene homopolymers may include. Exxon Mobil 3155 polypropylene, Exxon Mobil Achieve™ resins, and Total M3661 PP resin. Other examples of suitable propylene polymers are described in U.S. Pat. No. 6,500,563 to Datta, et al.; U.S. Pat. No. 5,539,056 to Yang, et al., and U.S. Pat. No. 5,596,052 to Resconi, et al.

Any of a variety of known techniques may generally be employed to form the olefin copolymers. For instance, olefin polymers may be formed using a free radical or a coordination catalyst (e.g., Ziegler-Natta). Preferably, the olefin polymer is formed from a single-site coordination catalyst, such as a metallocene catalyst. Such a catalyst system produces ethylene copolymers in which the comonomer is randomly distributed within a molecular chain and uniformly distributed across the different molecular weight fractions. Metallocene-catalyzed polyolefins are described, for instance, in U.S. Pat. No. 5,571,619 to McAlpin et al.; U.S. Pat. No. 5,322,728 to Davis et al.; U.S. Pat. No. 5,472,775 to Obijeski et al.; U.S. Pat. No. 5,272,236 to Lai et al.; and U.S. Pat. No. 6,090,325 to Wheat, et al. Examples of metallocene catalysts include bis(n-butylcyclopentadienyl)titanium dichloride, bis(n-butylcyclopentadienyl)zirconium dichloride bis(cyclopentadienyl)scandium chloride, bis(indenyl)zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl(cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, and so forth. Polymers made using metallocene catalysts typically have a narrow molecular weight range. For instance, metallocene-catalyzed polymers may have polydispersity numbers ($M_w/M_n$) of below 4, controlled short chain branching distribution, and controlled isotacticity.

B. Nanoinclusion Additive

As used herein, the term "nanoinclusion additive" generally refers to a material that is capable of being dispersed within the polymer matrix in the form of discrete domains of a nano-scale size. For example, prior to drawing, the domains may have an average cross-sectional dimension of from about 1 to about 1000 nanometers, in some embodiments from about 5 to about 800 nanometers, in some embodiments from about 10 to about 500 nanometers, and in some embodiments from about 20 to about 200 nanometers. The domains may have a variety of different shapes, such as elliptical, spherical, cylindrical, plate-like, tubular, etc. In one embodiment, for example, the domains have a substantially elliptical shape. The nanoinclusion additive is typically employed in an amount of from about 0.05 wt. % to about 20 wt. %, in some embodiments from about 0.1 wt. % to about 10 wt,%, and in some embodiments, from about 0.5 wt. % to about 5 wt. % of the thermoplastic composition, based on the weight of the continuous phase polyolefin matrix. The concentration of the nanoinclusion additive in the entire thermoplastic composition may likewise be from about 0.01 wt. % to about 15 wt. %, in some embodiments from about 0.05 wt. % to about 10 wt. % and in some embodiments, from about 0.3 wt. % to about 6 wt. % of the thermoplastic composition.

The nanoinclusion additive is partially incompatible with the polyolefin in the sense that it can be substantially uniformly distributed within the polyolefin matrix, but in the form of discrete domains. Such partial incompatibility can be accomplished in a variety of ways. In certain embodiments, for example, the nanoinclusion additive may possess a nonpolar component (e.g., olefin) that is compatible with the polyolefin matrix and allows it to become uniformly distributed therein. Nevertheless, the additive may also include a polar component that is incompatible with the polyolefin matrix, thereby allowing it to coalesce or segregate into discrete domains. Such a component may include low or high molecular weight polar molecular segments or blocks, ionic groups, charged or uncharged polar domains, and/or polar molecular groups. Alternatively, the additive may be entirely nonpolar in nature, but possess certain physical properties that still allow for discrete domains to be formed. For example, in certain embodiments, the nanoinclusion additive may be compatible or miscible with the polyolefin above a certain temperature, but phase separate at temperatures lower than the critical solution temperature. In this manner, the nanoinclusion additive can form a stable blend with the polyolefin in the melt phase, but as the temperature decreases, the continuous phase crystallizes and segregates so that the nanoinclusion additive can phase separate, coalesce, and form separate nano-scale domains.

The particular state or form of the nanoinclusion additive is not critical so long as the desired domains can be formed. For example, in some embodiments, the nanoinclusion additive can be in the form of a liquid or semi-solid at room temperature (e.g., 25° C.). Such a liquid can be readily dispersed in the matrix to form a metastable dispersion, and then quenched to preserve the domain size by reducing the temperature of the blend. The kinematic viscosity of such a liquid or semi-solid material is typically from about 0.7 to about 200 centistokes ("cs"), in some embodiments from about 1 to about 100 cs, and in some embodiments, from about 1.5 to about 80 cs, determined at 40° C. Suitable liquids or semi-solids may include, for instance, silicones, silicone-polyether copolymers, aliphatic polyesters, aromatic polyesters, alkylene glycols (e.g., ethylene glycol, diethylene glycol, triethylene glycol, tetraethylene glycol, propylene glycol, polyethylene glycol, polypropylene glycol, polybutylene glycol, etc.), alkane diols (e.g., 1,3-propanediol, 2,2-dimethyl-1,3-propanediol, 1,3-butanediol, 1,4-butanediol, 1,5-pentanediol, 1,6-hexanediol, 2,2,4-trimethyl-1,6 hexanediol, 1,3-cyclohexanedimethanol, 1,4-cyclohexanedimethanol, 2,2,4,4-tetramethyl-1,3-cyclobutanediol, etc.), amine oxides (e.g., octyldimethylamine oxide), fatty acid esters, fatty acid amides (e.g., oleamide, erucamide, stearamide, ethylene bis(stearamide), etc.), mineral, and vegetable oils, and so forth. One particularly suitable liquid or semi-solid is polyether polyol, such as commercially available under the trade name Pluriol® WI from BASF Corp.

In yet other embodiments, the nanoinclusion additive is in the form of a solid, which may be amorphous, crystalline, or semi-crystalline. For example, the nanoinclusion additive may be polymeric in nature and possess a relatively high molecular weight to help improve the melt strength and stability of the thermoplastic composition. As indicated above, the nanoinclusion additive is partially incompatible with the polyolefin matrix. One example of such an additive is a microcrystalline polyolefin wax, which is typically derived from ethylene and/or $C_3$-$C_{10}$-alk-1-enes, such as from propylene, 1-butene, 1-pentene, 1-hexene, 1-heptene, 1-octene, 1-nonene, and 1-decene. Microcrystalline waxes typically have a relatively low melting temperature, such as from about 30° C. to about 150° C., in some embodiments from about 50° C. to about 140° C., and in some embodiments, from about 80° C. to about 130° C. At such low melting temperatures the wax can form a miscible blend with the polyolefin when in the melt phase, but as the temperature decreases and polymer crystalizes or solidifies, the wax will segregate and coalesce forming separate nano-scale domains.

Another example of a polymeric nanoinclusion additive is a functionalized polyolefin that contains a polar and nonpolar component. The polar component may, for example, be provided by one or more functional groups and the nonpolar component may be provided by an olefin. The olefin component of the nanoinclusion additive may generally be formed from any linear or branched α-olefin monomer oligomer, or polymer (including copolymers) derived from an olefin monomer, such as described above. The functional group of the nanoinclusion additive may be any group, molecular segment and/or block that provides a polar component to the molecule and is not compatible with the polyolefin matrix polymer. Examples of molecular segment and/or blocks not compatible with polyolefin may include acrylates styrenics, polyesters, polyamides, etc. The functional group can have an ionic nature and comprise charged metal ions. Particularly suitable functional groups are maleic anhydride, maleic acid, fumaric acid, malemide, maleic acid hydrazide, a reaction product of maleic anhydride and diamine, methylnadic anhydride, dichloromaleic anhydride, maleic acid amide, etc. Maleic anhydride modified polyolefins are particularly suitable for use in the present invention. Such modified polyolefins are typically formed by grafting maleic anhydride onto a polymeric backbone material. Such maleated polyolefins are available from E. I. du Pont de Nemours and Company under the designation Fusabond®, such as the P Series (chemically modified polypropylene), E Series (chemically modified polyethylene), C Series (chemically modified ethylene vinyl acetate), A Series (chemically modified ethylene acrylate copolymers or terpolymers), or N Series (chemically modified ethylene-propylene, ethylene-propylene diene monomer ("EPDM") or ethylene-octene). Alternatively, maleated polyolefins are also available from Chemtura Corp under the designation Polybond®, Eastman Chemical Company under the designation Eastman G series, and Arkema under the designation Orevac®.

In certain embodiments, the polymeric nanoinclusion additive may also be reactive. One example of such a reactive nanoinclusion additive is a polyepoxide that contains, on average, at least two oxirane rings per molecule. Without intending to be limited by theory, it is believed that such polyepoxide molecules can undergo a reaction (e.g., chain extension, side chain branching, grafting, copolymer formation, etc.) with certain components of the composition to improve melt strength without significantly reducing glass transition temperature. The reactive additive can also provide compatibilization between the polyolefin and other more polar additives, such as microinclusion additives, and can improve the uniformity of dispersion and reduce the size of microinclusion additives. For example, as will be described in more detail below, certain embodiments of the present invention may employ a polyester as a microinclusion additive. In such embodiments, the reactive nanoinclusion additive may enable a nucleophilic ring-opening reaction via a carboxyl terminal group of the polyester (esterification) or via a hydroxyl group (etherification). Oxazoline side reactions may likewise occur to form esteramide moieties. Through such reactions, the molecular weight of a polyester microinclusion additive may be increased to counteract the degradation often observed during melt processing. The present inventors have discovered that too much of a reaction can lead to crosslinking between polymer backbones. If such crosslinking is allowed to proceed to a significant extent, the resulting polymer blend can become brittle and difficult to process into a material with the desired strength and elongation properties.

In this regard, the present inventors have discovered that polyepoxides having a relatively low epoxy functionality may be particularly effective, which may be quantified by its "epoxy equivalent weight". The epoxy equivalent weight reflects the amount of resin that contains one molecule of an epoxy group, and it may be calculated by dividing the number average molecular weight of the modifier by the number of epoxy groups in the molecule. The polyepoxide of the present invention typically has a number average molecular weight from about 7,500 to about 250,000 grams per mole, in some embodiments from about 15.000 to about 150,000 grams per mole, and in some embodiments, from about 20,000 to 100,000 grams per mole, with a polydispersity index typically ranging from 2.5 to 7. The polyepoxide may contain less than 50, in some embodiments from 5 to 45 and in some embodiments, from 15 to 40 epoxy groups. In turn, the epoxy equivalent weight may be less than about 15,000 grams per mole, in some embodiments from about 200 to about 10,000 grams per mole, and in some embodiments, from about 500 to about 7,000 grams per mole.

The polyepoxide may be a linear or branched, homopolymer or copolymer (e.g., random, graft, block, etc.) containing terminal epoxy groups, skeletal oxirane units, and/or pendent epoxy groups. The monomers employed to form such polyepoxides may vary. In one particular embodiment, for example, the polyepoxide contains at least one epoxy-functional (meth)acrylic monomeric component. As used herein, the term "(meth)acrylic" includes acrylic and methacrylic monomers, as well as salts or esters thereof, such as acrylate and methacrylate monomers. For example, suitable epoxy-functional (meth)acrylic monomers may include, but are not limited to, those containing 1,2-epoxy groups, such as glycidyl acrylate and glycidyl methacrylate. Other suitable epoxy-functional monomers include allyl glycidyl ether, glycidyl ethacrylate, and glycidyl itoconate.

The polyepoxide typically has a relatively high molecular weight, as indicated above, so that it may not only result in chain extension, but also help to achieve the desired blend morphology. The resulting melt flow rate of the polymer is thus typically within a range of from about 10 to about 200 grams per 10 minutes, in some embodiments from about 40 to about 150 grams per 10 minutes, and in some embodiments, from about 60 to about 120 grams per 10 minutes, determined at a load of 2160 grams and at a temperature of 190° C.

The polyepoxide also typically includes at least one linear or branched α-olefin monomer, such as those having from 2 to 20 carbon atoms and preferably from 2 to 8 carbon atoms. Specific examples include ethylene, propylene 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Particularly desired α-olefin comonomers are ethylene and propylene. Another suitable monomer may include a (meth)acrylic monomer that is not epoxy-functional. Examples of such (meth)acrylic monomers may include methyl acrylate, ethyl acrylate, n-propyl acrylate, i-propyl acrylate, n-butyl acrylate, s-butyl acrylate, i-butyl acrylate, t-butyl acrylate, n-amyl acrylate, i-amyl acrylate, isobornyl acrylate, n-hexyl acrylate, 2-ethylbutyl acrylate, 2-ethylhexyl acrylate, n-octyl acrylate, n-decyl acrylate, methylcyclohexyl acrylate, cyclopentyl acrylate, cyclohexyl acrylate, methyl methacrylate, ethyl methacrylate, 2-hydroxyethyl methacrylate, n-propyl methacrylate, n-butyl methacrylate, i-propyl methacrylate, i-butyl methacrylate, n-amyl methacrylate, n-hexyl methacrylate, i-amyl methacrylate, s-butyl-methacrylate, t-butyl methacrylate, 2-ethylbutyl methacrylate, methylcyclohexyl methacrylate, cinnamyl methacrylate, crotyl methacrylate, cyclohexyl methacrylate, cyclopentyl methacrylate, 2-ethoxyethyl methacrylate, isobornyl methacrylate etc., as well as combinations thereof.

In one particularly desirable embodiment of the present invention, the polyepoxide is a terpolymer formed from an epoxy-functional (meth)acrylic monomeric component, α-olefin monomer component, and non-epoxy functional (meth)acrylic monomeric component. For example, the polyepoxide may be poly(ethylene-co-methylacrylate-co-glyciclyl methacrylate), which has the following structure:

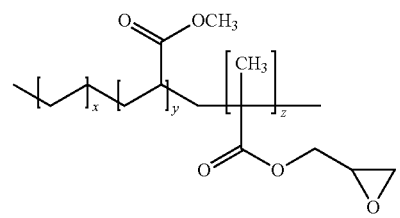

wherein, x, y, and z are 1 or greater.

The epoxy functional monomer may be formed into a polymer using a variety of known techniques. For example, a monomer containing polar functional groups may be grafted onto a polymer backbone to form a graft copolymer.

Such grafting techniques are well known in the art and described, for instance, in U.S. Pat. No. 5,179,164. In other embodiments, a monomer containing epoxy functional groups may be copolymerized with a monomer to form a block or random copolymer using known free radical polymerization techniques, such as high pressure reactions, Ziegler-Natta catalyst reaction systems, single site catalyst (e.g., metallocene) reaction systems, etc.

The relative portion of the monomeric component(s) may be selected to achieve a balance between epoxy-reactivity and melt flow rate. More particularly, high epoxy monomer contents can result in good reactivity, but too high of a content may reduce the melt flow rate to such an extent that the polyepoxide adversely impacts the melt strength of the polymer blend. Thus, in most embodiments, the epoxy-functional (meth)acrylic monomer(s) constitute from about 1 wt. % to about 25 wt. %, in some embodiments from about 2 wt. % to about 20 wt. %, and in some embodiments, from about 4 wt. % to about 15 wt % of the copolymer. The $\alpha$-olefin monomer(s) may likewise constitute from about 55 wt. % to about 95 wt. %, in some embodiments from about 60 wt. % to about 90 wt. %, and in some embodiments, from about 65 wt. % to about 85 wt. % of the copolymer. When employed, other monomeric components (e.g., non-epoxy functional (meth)acrylic monomers) may constitute from about 5 wt. % to about 35 wt. %, in some embodiments from about 8 wt. % to about 30 wt. %, and in some embodiments, from about 10 wt. % to about 25 wt. % of the copolymer. One specific example of a suitable polyepoxide that may be used in the present invention is commercially available from Arkema under the name LOTADER® AX8950 or AX8900. LOTADER® AX8950, for instance, has a melt flow rate of 70 to 100 g/10 min and has a glycidyl methacrylate monomer content of 7 wt. % to 11 wt. %, a methyl acrylate monomer content of 13 wt. % to 17 wt. %, and an ethylene monomer content of 72 wt. % to 80 wt. %. Another suitable polyepoxide is commercially available from DuPont under the name ELVALOY® PTW, which is a terpolymer of ethylene, butyl acrylate, and glycidyl methacrylate and has a melt flow rate of 12 g/10 min.

In addition to controlling the type and relative content of the monomers used to form the polyepoxide, the overall weight percentage may also be controlled to achieve the desired benefits. For example, if the modification level is too low, the desired increase in melt strength and mechanical properties may not be achieved. The present inventors have also discovered, however, that if the modification level is too high, processing may be restricted due to strong molecular interactions (e.g., crosslinking) and, physical network formation by the epoxy functional groups. Thus, the polyepoxide is typically employed in an amount of from about 0.05 wt. % to about 10 wt. %, in some embodiments from about 0.1 wt. % to about 8 wt. %, in some embodiments from about 0.5 wt. % to about 5 wt. %, and in some embodiments from about 1 wt. % to about 3 wt. % based on the weight of the polyolefins employed in the composition. The polyepoxide may also constitute from about 0.05 wt. % to about 10 wt. %, in some embodiments from about 0.05 wt. % to about 8 wt. %, in some embodiments from about 0.1 wt. % to about 5 wt. % and in some embodiments, from about 0.5 wt. % to about 3 wt. %, based on the total weight of the composition.

Other reactive nanoinclusion additives may also be employed in the present invention, such as oxazoline-functionalized polymers, cyanide-functionalized polymers, etc. When employed, such reactive nanoinclusion additives may be employed within the concentrations noted above for the polyepoxide. In one particular embodiment, an oxazoline-grafted polyolefin may be employed that is a polyolefin grafted with an oxazoline ring-containing monomer. The oxazoline may include a 2-oxazoline, such as 2-vinyl-2-oxazoline (e.g., 2-isopropenyl-2-oxazoline), 2-fatty-alkyl-2-oxazoline (e.g., obtainable from the ethanolamide of oleic acid, linoleic acid, palmitoleic acid, gadoleic acid, erucic acid and/or arachidonic acid) and combinations thereof. In another embodiment, the oxazoline may be selected from ricinoloxazoline maleinate, undecyl-2-oxazoline, soya-2-oxazoline, ricinus-2-oxazoline and combinations thereof, for example. In yet another embodiment, the oxazoline is selected from 2-isopropenyl-2-oxazoline, 2-isopropenyl-4,4-dimethyl-2-oxazoline and combinations thereof.

In certain embodiments of the present invention, multiple nanoinclusion additives may be employed in combination. For instance, a first nanoinclusion additive (e.g., polyepoxide) may be dispersed in the form of domains having an average cross-sectional dimension of from about 50 to about 500 nanometers, in some embodiments from about 60 to about 400 nanometers, and in some embodiments from about 80 to about 300 nanometers. A second nanoinclusion additive may also be dispersed in the form of domains that are smaller than the first nanoinclusive additive, such as those having an average cross-sectional dimension of from about 1 to about 50 nanometers, in some embodiments from about 2 to about 45 nanometers, and in some embodiments from about 5 to about 40 nanometers. When employed, the first and/or second nanoinclusion additives typically constitute from about 0.05 wt. % to about 20 wt. %, in some embodiments from about 0.1 wt. % to about 10 wt. %, and in some embodiments, from about 0.5 wt. % to about 5 wt. % of the thermoplastic composition, based on the weight of the continuous phase (matrix polymer(s)). The concentration of the first and/or second nanonclusion additives in the entire thermoplastic composition may likewise be from about 0.01 wt. % to about 15 wt. %, in some embodiments from about 0.05 wt. % to about 10 wt. %, and in some embodiments, from about 0.1 wt. % to about 8 wt. % of the thermoplastic composition.

Nanofillers may optionally be employed for the second nanoinclusion additive, examples of which may include carbon black, carbon nanotubes, carbon nanofibers, nanoclays metal nanoparticles, nanosilica, nanoalumina, etc. Nanoclays are particularly suitable. The term "nanoclay" generally refers to nanoparticles of a clay material (a naturally occurring mineral, an organically modified mineral, or a synthetic nanomaterial), which typically have a platelet structure. Examples of nanoclays include, for instance, montmorillonite (2:1 layered smectite clay structure), bentonite (aluminium phyllosilicate formed primarily of montmorillonite), kaolinite (1:1 aluminosilicate having a platy structure and empirical formula of $Al_2Si_2O_5(OH)_4$), halloysite (1:1 aluminosilicate having a tubular structure and empirical formula of $Al_2Si_2O_5(OH)_4$), etc. An example of a suitable nanoclay is Cloisite®, which is a montmorillonite nanoclay and commercially available from Southern Clay Products, Inc. Other examples of synthethic nanoclays include but are not limited to a mixed-metal hydroxide nanoclay, layered double hydroxide nanoclay (e.g., sepiocite), laponite, hectorite, saponite, indonite, etc.

If desired, the nanoclay may contain a surface treatment to help improve compatibility with the matrix polymer (e.g., polyester). The surface treatment may be organic or inorganic. In one embodiment, an organic surface treatment is employed that is obtained by reacting an organic cation with the clay. Suitable organic cations may include, for instance, organoquaternary ammonium compounds that are capable of exchanging cations with the clay, such as dimethyl bis[hydrogenated tallow] ammonium chloride (2M2HT), methyl benzyl bis[hydrogenated tallow] ammonium chloride (MB2HT), methyl tris[hydrogenated tallow alkyl] chloride (M3HT), etc. Examples of commercially available organic nanoclays may include, for instance, Dellite® 43B (Laviosa Chimica of Livorno, Italy), which is a montmorillonite clay modified with dimethyl benzylhydrogenated tallow ammonium salt. Other examples include Closite® 25A and Cloisite® 30B (Southern Clay Products) and Nanofil 919 (Süd Chemie). If desired, the nanofiller can be blended with a carrier resin to form a masterbatch that enhances the compatibility of the additive with the other polymers in the composition. Particularly suitable carrier resins include, for instance, polyesters (e.g., polylactic acid, polyethylene terephthalate, etc.); polyolefins (e.g., ethylene polymers, propylene polymers etc.); and so forth, as described in more detail above.

Regardless of the material employed, the nanoinclusion additive is typically selected to have a certain viscosity (or melt flow rate) to ensure that the discrete domains and resulting pores can be adequately maintained. For example, if the viscosity of the nanoinclusion additive is too low (or melt flow rate is too high), it tends to flow and disperse uncontrollably through the continuous phase. This results in lamellar, plate-like domains or co-continuous phase structures that are difficult to maintain and also likely to prematurely fracture. Conversely, if the viscosity is too high (or melt flow rate is too low), it tends to clump together and form very large elliptical domains which are difficult to disperse during blending. This may cause uneven distribution of the nanoinclusion additive through the entirety of the continuous phase. For instance, the ratio of the melt flow rate of the polyolefin to the melt flow rate of a polymeric nanoinclusion additive, for instance, may be from about 0.2 to about 8, in some embodiments from about 0.5 to about 6, and in some embodiments, from about 1 to about 5. The nanoinclusion additive may, for example, have a melt flow rate (on a dry basis) of from about 0.1 to about 100 grams per 10 minutes, in some embodiments from about 0.5 to about 50 grams per 10 minutes, and in some embodiments from about 5 to about 15 grams per 10 minutes, determined at a load of 2160 grams and at a temperature at least about 40° C. above the melting temperature (e.g., at 190° C.) in accordance with ASTM D1238 The polyolefin may likewise have a melt flow rate (on a dry basis) of from about 0.5 to about 80 grams per 10 minutes in some embodiments from about 1 to about 40 grams per 10 minutes, and in some embodiments from about 5 to about 20 grams per 10 minutes, determined at a load of 2160 grams and at a temperature at least about 40° C. above the melting temperature (e.g. at 230° C.) in accordance with ASTM D1238.

C. Microinclusion Additive

Although not required, the composition of the present invention may also employ a microinclusion additive. As used herein, the term "microinclusion additive" generally refers to any material that is capable of being dispersed within the polymer matrix in the form of discrete domains of a micro-scale size. For example, prior to drawing, the domains may have an average cross-sectional dimension of from about 0.1 µm to about 25 µm, in some embodiments from about 0.5 µm to about 20 µm, and in some embodiments from about 1 µm to about 10 µm. When employed, the present inventors have discovered that the micro-scale and nano-scale phase domains are able to interact in a unique manner when subjected to a deformation and elongational strain (e.g., drawing) to create a network of pores. Namely, it is believed that elongational strain can initiate intensive localized shear zones and/or stress intensity zones (e.g., normal stresses) near the micro-scale discrete phase domains as a result of stress concentrations that arise from the incompatibility of the materials. These shear and/or stress intensity zones cause some initial debonding in the polyolefin matrix adjacent to the micro-scale domains. Notably, however, the localized shear and/or stress intensity zones created near the nano-scale discrete phase domains may overlap with the micro-scale zones to cause even further debonding to occur in the polymer matrix, thereby creating a substantial number of nanopores adjacent to the nano-scale domains and/or micro-scale domains.

The particular nature of the microinclusion additive is not critical, and may include liquids, semi-solids, or solids (e.g., amorphous, crystalline, or semi-crystalline). In certain embodiments, the microinclusion additive is polymeric in nature and, possesses, a relatively high molecular weight to help improve the melt strength and stability of the thermoplastic composition. Typically, the microinclusion additive polymer may be generally incompatible with the matrix polymer. In this manner, the additive can better become dispersed as discrete phase domains within a continuous phase of the matrix polymer. The discrete domains are capable of absorbing energy that arises from an external force, which increases the overall toughness and strength of the resulting material. The domains may have a variety of different shapes, such as elliptical, spherical, cylindrical, plate-like, tubular, etc. In one embodiment, for example, the domains have a substantially elliptical shape. The physical dimension of an individual domain is typically small enough to minimize the propagation of cracks through the polymeric material upon the application of an external stress, but large enough to initiate microscopic plastic deformation and allow for shear zones at and around particle inclusions.

The microinclusion additive may have a certain melt flow rate (or viscosity) to ensure that the discrete domains and resulting pores can be adequately maintained. For example, if the melt flow rate of the additive is too high, it tends to flow and disperse uncontrollably through the continuous phase. This results in lamellar, plate-like domains or co-continuous phase structures that are difficult to maintain and also likely to prematurely fracture. Conversely, if the melt flow rate of the additive is too low, it tends to clump together and form very large elliptical domains, which are difficult to disperse during blending. This may cause uneven distribution of the additive through the entirety of the continuous phase. In this regard, the present inventors have discovered that the ratio of the melt flow rate of the microinclusion additive to the melt flow rate of the matrix polymer is typically from about 0.5 to about 10, in some embodiments from about 1 to about 8, and in some embodiments, from about 2 to about 6. The microinclusion additive may, for example, have a melt flow rate of from about 5 to about 200 grams per 10 minute in some embodiments from about 20 to about 160 grams per 10 minutes, and in some embodiments, from about 40 to about 100 grams per 10 minutes, determined at a load of 2160 grams and at a temperature at least about 40° C. above its melting temperature (e.g., 210° C.).

In addition to the properties noted above, the mechanical characteristics of the microinclusion additive may also be selected to achieve the desired porous network. For example, applied with an external force, stress concentrations (e.g., including normal or shear stresses) and shear and/or plastic yielding zones may be initiated at and around the discrete phase domains as a result of stress concentrations that arise from a difference in the elastic modulus of the additive and matrix polymer. Larger stress concentrations promote more intensive localized plastic flow at the domains, which allows them to become significantly elongated when stresses are imparted. These elongated domains can allow the composition to exhibit a more pliable and softer behavior. To enhance the stress concentrations, the microinclusion additive may be selected to have a relatively high Young's modulus of elasticity in comparison to the polyolefin matrix. For example, the ratio of the modulus of elasticity of the additive to that of polyolefin matrix is typically from about 1 to about 250, in some embodiments from about 2 to about 100, and in some embodiments, from about 2 to about 50. The modulus of elasticity of the microinclusion additive may, for instance, range from about 200 to about 3,500 Megapascals (MPa), in some embodiments from about 300 to about 2,000 MPa, and in some embodiments from about 400 to about 1,500 MPa. To the contrary, the modulus of elasticity of the polyolefin may, for instance, range from about 100 to about 1,500 MPa, and in some embodiments, from about 200 to about 1000 MPa. Alternatively, the modulus of elasticity of microinclusion additive can be lower than the modulus of elasticity of polyolefin matrix. The modulus of elasticity may, for example, range from about 10 MPa to about 100 MPa, and optionally from about 20 MPA to about 80 MPa.

While a wide variety of microinclusion additives may be employed that have the properties identified above, particularly suitable examples of such additives may include styrenic copolymers (e.g., styrene-butadiene-styrene, styrene-isoprene-styrene, styrene-ethylene-propylene-styrene, styrene-ethylene butadiene-styrene, etc.); fluoropolymers, such as polyvinyl chloride (PVC), polytetrafluoroethylene (PTFE), polychlorotrifluoroethylene (PCTFE), etc.; polyvinyl alcohols; polyvinyl acetates; polyesters, such as aliphatic polyesters, such as polycaprolactone, polyesteramides, polylactic acid (PLA) and its copolymers, polyglycolic acid, polyalkylene carbonates (e.g., polyethylene carbonate), poly-3-hydroxybutyrate (PHB), poly-3-hydroxyvalerate (PHV), poly-3-hydroxybutyrate-co-4-hydroybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.), aliphatic-aromatic copolyesters (e.g., polybutylene adipate terephthalate, polyethylene adipate terephthalate, polyethylene adipate isophthalate, polybutylene adipate isophthalate, etc.), aromatic polyesters (e.g., polyethylene terephthalate, polybutylene terephthalate, etc.); and so forth.

Particularly suitable are microinclusion additives that are generally rigid in nature to the extent that they have a relatively high glass transition temperature. For example, the glass transition temperature ("$T_g$") may be about 0° C. or more, in some embodiments from about 5° C. to about 100° C., in some embodiments from about 30° C. to about 80° C. and in, some embodiments, from about 50° C. to about 75° C. The glass transition temperature may be determined by dynamic mechanical analysis in accordance with ASTM E1640-09.

One particularly suitable rigid polyester is polylactic acid, which may generally be derived from monomer units of any isomer of lactic acid, such as levorotory-lactic acid ("L-lactic acid"), dextrorotatory-lactic acid ("D-lactic acid"), meso-lactic acid, or mixtures thereof. Monomer units may also be formed from anhydrides of any isomer of lactic acid, including L-lactide, D-lactide, meso-lactide, or mixtures thereof. Cyclic dimers of such lactic acids and/or lactides may also be employed. Any known polymerization method, such as polycondensation or ring-opening polymerization may be used to polymerize lactic acid. A small amount of a chain-extending agent (e.g., a diisocyanate compound, an epoxy compound or an acid anhydride) may also be employed. The polylactic acid may be a homopolymer or a copolymer, such as one that contains monomer units derived from L-lactic acid and monomer units derived from D-lactic acid. Although not required, the rate of content of one of the monomer unit derived from L-lactic acid and the monomer unit derived from D-lactic acid is preferably about 85 mole % or more, in some embodiments about 90 mole % or more, and in some embodiments, about 95 mole % or more. Multiple polylactic acids, each having a different ratio between the monomer unit derived from L-lactic acid and the monomer unit derived from D-lactic acid, may be blended at an arbitrary percentage. Of course, polylactic acid may also be blended with other types of polymers (e.g., polyolefins, polyesters, etc.).

In one particular embodiment, the polylactic acid has the following general structure:

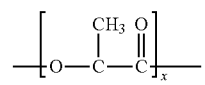

One specific example of a suitable polylactic acid polymer that may be used in the present invention is commercially available from Biomer, Inc. of Krailling, Germany) under the name BIOMER™ L9000. Other suitable polylactic acid polymers are commercially available from Natureworks LLC of Minnetonka, Minn. (NATUREWORKS®) or Mitsui Chemical (LACEA™). Still other suitable polylactic acids may be described in U.S. Pat. Nos. 4,797,468; 5,470,944; 5,770,682; 5,821,327; 5,880,254; and 6,326,458, which are incorporated herein in the entirety by reference thereto for all purposes.

The polylactic acid typically has a number average molecular weight ("$M_n$") ranging from about 40,000 to about 180,000 grams per mole, in some embodiments from about 50,000 to about 160,000 grams per mole, and in some embodiments, from about 80,000 to about 120,000 grams per mole. Likewise, the polymer also typically has a weight average molecular weight ("$M_w$") ranging from about 80,000 to about 250,000 grams per mole, in some embodiments from about 100,000 to about 200,000 grams per mole, and in some embodiments, from about 110,000 to about 160,000 grams per mole. The ratio of the weight average molecular weight to the number average molecular weight ("$M_w/M_n$"), i.e., the "polydispersity index", is also relatively low. For example, the polydispersity index typically ranges from about 1.0 to about 3.0, in some embodiments from about 1.1 to about 2.0, and in some embodiments, from about 1.2 to about 1.8. The weight and number average molecular weights may be determined by methods known to those skilled in the art.

Some types of neat polyesters (e.g., polylactic acid) can absorb water from the ambient environment such that it has a moisture content of about 500 to 600 parts per million ("ppm"), or even greater, based on the dry weight of the starting polylactic acid. Moisture content may be determined in a variety of ways as is known in the art, such as in accordance with ASTM D 7191-05, such as described below. Because the presence of water during melt processing can hydrolytically degrade the polyester and reduce its molecular weight, it is sometimes desired to dry the polyester prior to blending. In most embodiments, for example, it is desired that the renewable polyester have a moisture content of about 300 parts per million ("ppm") or less, in some embodiments about 200 ppm or less, in some embodiments from about 1 to about 100 ppm prior to blending with the microinclusion additive. Drying of the polyester may occur, for instance, at a temperature of from about 50° C. to about 100° C. and in some embodiments, from about 70° C. to about 80° C.

Regardless of the materials employed, the relative percentage of the microinclusion additive in the thermoplastic composition is selected to achieve the desired properties without significantly impacting the resulting composition. For example, the microinclusion additive is typically employed in an amount of from about 1 wt. % to about 30 wt. %, in some embodiments from about 2 wt. % to about 25 wt. %, and in some embodiments from about 5 wt. % to about 20 wt. % of the thermoplastic composition, based on the weight of the polyolefin matrix employed in the composition. The concentration of the microinclusion additive in the entire thermoplastic composition may likewise constitute from about 0.1 wt. % to about 30 wt. %, in some embodiments from about 0.5 wt. % to about 25 wt. %, and in some embodiments, from about 1 wt. % to about 20 wt. %.

D. Other Components

A wide variety of ingredients may be employed in the composition for a variety of different reasons. For instance, in one particular embodiment, an interphase modifier may be employed in the thermoplastic composition to help reduce the degree of friction and connectivity between the nanoinclusion and/or microinclusion additives and polyolefin matrix, and thus enhance the degree and uniformity of debonding. In this manner, the pores can become distributed in a more homogeneous fashion throughout the composition. The modifier may be in a liquid or semi-solid form at room temperature (e.g., 25° C.) so that it possesses a relatively low viscosity, allowing it to be more readily incorporated into the thermoplastic composition and to easily migrate to the polymer surfaces. By reducing physical forces at the interfaces of the polyolefin matrix and the additive, it is believed that the low viscosity, hydrophobic nature of the modifier can help facilitate debonding. As used herein, the term "hydrophobic" typically refers to a material having a contact angle of water in air of about 40° or more, and in some cases, about 60° or more. In contrast, the term "hydrophilic" typically refers to a material having a contact angle of water in air of less than about 40°. One suitable test for measuring the contact angle is ASTM D5725-99 (2008).

Although not required, the interphase modifier may be particularly suitable n embodiments in which a microinclusion additive is employed and in which the nanoinclusion additive is a solid (e.g., polymeric material). Suitable hydrophobic, low viscosity interphase modifiers may include, for instance, the liquids and/or semi-solids referenced above. One particularly suitable interphase modifier is polyether polyol, such as commercially available under the trade name PLURIOL® WI from BASF Corp. Another suitable modifier is a partially renewable ester, such as commercially available under the trade name HALLGREEN® IM from Hallstar.

When employed, the interphase modifier may constitute from about 0.1 wt. % to about 20 wt. %, in some embodiments from about 0.5 wt. % to about 15 wt. %, and in some embodiments, from about 1 wt. % to about 10 wt. % of the thermoplastic composition, based on the weight of the continuous phase polyolefin matrix. The concentration of the interphase modifier in the entire thermoplastic composition may likewise constitute from about 0.05 wt. % to about 20 wt. %, in some embodiments from about 0.1 wt. % to about 15 wt. %, and in some embodiments, from about 0.5 wt. % to about 10 wt. %. In the amounts noted above, the interphase modifier has a character that enables it to readily migrate to the interfacial surface of the polymers and facilitate debonding without disrupting the overall melt properties of the thermoplastic composition. For example, the melt flow rate of the thermoplastic composition may also be similar to that of the polyolefin matrix. For example, the melt flow rate of the composition (on a dry basis) may be from about 0.1 to about 250 grams per 10 minutes, in some embodiments from about 0.5 to about 200 grams per 10 minutes, and in some embodiments, from about 5 to about 150 grams per 10 minutes, determined at a load of 2160 grams and at 190° C. in accordance with ASTM D1238.

Compatibilizers may also be employed that improve interfacial adhesion and reduce the interfacial tension between the domain and the matrix, thus allowing the formation of smaller domains during mixing. Examples of suitable compatibilizers may include, for instance, copolymers functionalized with epoxy or maleic anhydride chemical moieties. An example of a maleic anhydride compatibilizer is polypropylene-grafted-maleic anhydride, which is commercially available from Arkema under the trade names Orevac™ 18750 and Orevac™ CA 100. When employed compatibilizers may constitute from about 0.05 wt. % to about 10 wt. %, in some embodiments from about 0.1 wt. % to about 8 wt. %, and in some embodiments, from about 0.5 wt. % to about 5 wt. % of the thermoplastic composition, based on the weight of the continuous phase polyolefin matrix.

Other suitable materials that may also be used in the thermoplastic composition, such as catalysts, antioxidants, stabilizers, surfactants, waxes, solid solvents, nucleating agents, particulates, nanofillers, and other materials added to enhance the processability and mechanical properties of the thermoplastic composition. Nevertheless, one beneficial aspect of the present invention is that good properties may be provided without the need for various conventional additives, such as blowing agents (e.g., chlorofluorocarbons, hydrochlorofluorocarbons, hydrocarbons, carbon dioxide, supercritcal carbon dioxide, nitrogen, etc.) and pore-initiating inorganic oxide fillers (e.g., calcium carbonate). In fact, the thermoplastic composition may be generally free of blowing agents and/or pore-initiating inorganic, oxide fillers, which are conventionally required to form microporous films. This can provide numerous benefits, including a potential reduction in costs and manufacturing complexity. In fact, the thermoplastic composition and/or one or more layers of the film (e.g., base layer) may be generally free of such blowing agents and/or fillers (e.g., calcium carbonate) may be present in an amount of no more than about 1 wt. %, in some embodiments no more than about 0.5 wt. %, and in some embodiments, from about 0.001 wt. % to about 0.2 wt. % of the thermoplastic composition. Nevertheless, in certain embodiments, higher amounts of blowing agents and/or fillers may be employed in the thermoplastic composition if so desired. Further, due to its stress whitening properties, as described in more detail below, the resulting composition may achieve an opaque color (e.g., white) without the need for conventional pigments, such as titanium dioxide. In certain embodiments, for example, pigments may be present in an amount of no more than about 1 wt. %, in some embodiments no more than about 0.5 wt. %, and in some embodiments, from about 0.001 wt. % to about 0.2 wt. % of the thermoplastic composition.

II. Blending

To form the thermoplastic composition, the components are typically blended together using any of a variety of known techniques. In one embodiment, for example, the components may be supplied separately or in combination. For instance, the components may first be dry mixed together to form an essentially homogeneous dry mixture, and they may likewise be supplied either simultaneously or in sequence to a melt processing device that dispersively blends the materials. Batch and/or continuous melt processing techniques may be employed. For example, a mixer/kneader, Banbury mixer, Farrel continuous mixer, single-screw extruder, twin-screw extruder, roll mill, etc., may be utilized to blend and melt process the materials. Particularly suitable melt processing devices may be a co-rotating, twin-screw extruder (e.g., ZSK-30 extruder available from Werner & Pfleiderer Corporation of Ramsey, N.J. or a Thermo Prism™ USALAB 16 extruder available from Thermo Electron Corp., Stone, England). Such extruders may include feeding and venting ports and provide high intensity distributive and dispersive mixing. For example, the components may be fed to the same or different feeding ports of the twin-screw extruder and melt blended to form a substantially homogeneous melted mixture. If desired, other additives may also be injected into the polymer melt and/or separately fed into the extruder at a different point along its length.

Regardless of the particular processing technique chosen, the resulting melt blended composition typically contains nano-scale domains of the nanoinclusion additive and optionally micro-scale domains of the microinclusion additive. The degree of shear/pressure and heat may be controlled to ensure sufficient dispersion, but not so high as to adversely reduce the size of the domains so that they are incapable of achieving the desired properties. For example, blending typically occurs at a temperature of from about 180° C. to about 300° C. in some embodiments from about 185° C. to about 250° C., and in some embodiments, from about 190° C. to about 240° C. Likewise, the apparent shear rate during melt processing may range from about 10 seconds$^{-1}$ to about 3000 seconds$^{-1}$, in some embodiments from about 50 seconds$^{-1}$ to about 2000 seconds$^{-1}$, and in some embodiments, from about 100 seconds$^{-1}$ to about 1200 seconds$^{-1}$. The apparent shear rate may be equal to 4 $Q/\pi R^3$, where Q is the volumetric flow rate ("m$^3$/s") of the polymer melt and R is the radius ("m") of the capillary (e.g., extruder die) through which the melted polymer flows. Of course, other variables, such as the residence time during melt processing, which is inversely proportional to throughput rate may also be controlled to achieve the desired degree of homogeneity.

To achieve the desired shear conditions (e.g., rate, residence time, shear rate, melt processing temperature, etc.), the speed of the extruder screw(s) may be selected with a certain range. Generally, an increase in product temperature is observed with increasing screw speed due to the additional mechanical energy input into the system. For example, the screw speed may range from about 50 to about 600 revolutions per minute ("rpm"), in some embodiments from about 70 to about 500 rpm, and in some embodiments, from about 100 to about 300 rpm. This may result in a temperature that is sufficiently high to disperse the nanoinclusion additive without adversely impacting the size of the resulting domains. The melt shear rate, and in turn the degree to which the additives are dispersed, may also be increased through the use of one or more distributive and/or dispersive mixing elements within the mixing section of the extruder. Suitable distributive mixers for single screw extruders may include, for instance, Saxon, Dulmage, Cavity Transfer mixers, etc. Likewise, suitable dispersive mixers ay include Blister ring, Leroy/Maddock, CRD mixers, etc. As is well known in the art, the mixing may be further improved by using pins in the barrel that create a folding and reorientation of the polymer melt, such as those used n Buss Kneader extruders, Cavity Transfer mixers, and Vortex Intermeshing Pin (VIP) mixers.

III. Film Construction

Any known technique may be used to form a film from the composition, including blowing, casting, flat die extruding, etc. In one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al. In yet another embodiment, however, the film is formed using a casting technique.

Referring to FIG. 1, for instance, one embodiment of a method for forming a cast film is shown. In this embodiment, the raw materials (not shown) are supplied to the extruder 80 from a hopper 40 and then cast onto a casting roll 90 to form a single-layered precursor film 10a. If a multilayered film is to be produced, the multiple layers are co-extruded together onto the casting roll 90. The casting roll 90 may optionally be provided with embossing elements to impart a pattern to the film. Typically, the casting roll 90 is kept at temperature sufficient to solidify and quench the sheet 10a as it is formed such as from about 10 to 60° C. If desired, vacuum box may be positioned adjacent to the casting roll 90 to help keep the precursor film 10a close to the surface of the roll 90. Additionally, air knives or electrostatic pinners may help force the precursor film 10a against the surface of the casting roll 90 as it moves around a spinning roll. An air knife is a device known in the art that focuses a stream of air a very high flow rate to pin the edges of the film.

Once cast, the film 10a may then be optionally oriented in one or more directions to further improve film uniformity. The film may be immediately reheated to a temperature below the melting point of one or more polymers in the film, but high enough to enable the composition to be drawn or stretched. In the case of sequential orientation, the "softened" film is drawn by rolls rotating at different speeds of rotation such that the sheet is stretched to the desired draw ratio in the longitudinal direction (machine direction). This "uniaxially" oriented film may then be optionally laminated to a fibrous web. In addition, the uniaxially oriented film may also be oriented in the cross-machine direction to form a "biaxially oriented" film. For example, the film may be clamped at its lateral edges by chain clips and conveyed into a tenter oven. In the tenter oven, the film may be reheated and drawn in the cross-machine direction to the desired draw ratio by chain clips diverged in their forward travel.

Referring again to FIG. 1, for instance, one method for forming a uniaxially oriented film is shown. As illustrated, the precursor film 10a is directed to a film-orientation unit 100 or machine direction orienter ("MDO"), such as commercially available from Marshall and Willams, Co. of Providence, R.I. The MDO has a plurality of stretching rolls (such as from 5 to 8) which progressively stretch and thin the film in the machine direction, which is the direction of travel of the film through the process as shown in FIG. 1. While the MDO 100 is illustrated with eight rolls, it should be understood that the number of rolls may be higher or lower, depending on the level of stretch that is desired and the degrees of stretching between each roll. The film may be stretched in either single or multiple discrete stretching operations. It should be noted that some of the rolls in an MDO apparatus may not be operating at progressively higher speeds. If desired, some of the rolls of the MDO 100 may act as preheat rolls. If present, these first few rolls heat the film 10a above room temperature (e.g. to 125° F.). The progressively faster speeds of adjacent rolls in the MDO act to stretch the film 10a. The rate at which the stretch rolls rotate determines the amount of stretch in the film and final film weight.

The resulting film 10b may then be wound and stored on a take-up roll 60. While not shown here, various additional potential processing and/or finishing steps known in the art, such as slitting, treating, aperturing, printing graphics, or lamination of the film with other layers (e.g., nonwoven web materials), may be performed without departing from the spirit and scope of the invention.

The film of the present invention may be mono- or multi-layered (e.g., from 2 to 20 layers, and in some embodiments, from 3 to 10 layers). For example, a multi-layered film may contain at least one core layer that is positioned adjacent to at least one outer layer. Outer layers are often used for heat sealing or printing. In one embodiment, for example, it may be desirable to employ first and second outer layers that sandwich the core layer. The core layer(s) typically constitute a substantial portion of the weight of the film such as from about 50 wt. % to about 99 wt. %, in some embodiments from about 55 wt. % to about 90 wt. %, and in some embodiments, from about 60 wt. % to about 85 wt. % of the film. The outer layer(s) may likewise constitute from about 1 wt. % to about 50 wt. %, in some embodiments about 10 wt. % to about 45 wt. %, and in some embodiments, from about 15 wt. % to about 40 wt. % of the film.

The thermoplastic composition of the present invention may be employed in any layer of the film, including the core layer and/or the outer layer. In one embodiment, for example, the core layer is formed from the composition of the present invention and the outer layer(s) are formed from the composition or from an additional polymer material. Likewise, in other possible embodiments, one or more of the outer layers are formed from the composition of the present invention and the core layer is formed from an additional polymer material. When employed, the additional material may include any type of polymer, such as polyolefins (e.g., polyethylene, polypropylene, etc.), polyesters, polyamides, styrenic copolymers, polyurethanes, polyvinyl acetate, polyvinyl alcohol, etc.

If desired, the film may also be laminated to one or more nonwoven web facings to reduce the coefficient of friction and enhance the cloth-like feel of the composite surface. Exemplary polymers for use in forming nonwoven web facings may include, for instance, polyolefins, e.g., polyethylene, polypropylene, polybutylene, etc.; polytetrafluoroethylene; polyesters, e.g., polyethylene terephthalate and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; polyurethanes; polylactic acid; copolymers thereof; and so forth. If desired, renewable polymers, such as those described above, may also be employed. Synthetic or natural cellulosic polymers may also be used, including but not limited to, cellulosic esters; cellulosic ethers; cellulosic nitrates; cellulosic acetates; cellulosic acetate butyrates; ethyl cellulose; regenerated celluloses, such as viscose, rayon, and so forth. It should be noted that the polymer(s) may also contain other additives such as processing aids or treatment compositions to impart desired properties to the fibers, residual amounts of solvents, pigments or colorants, and so forth.

Monocomponent and/or multicomponent fibers may be used to form the nonwoven web facing. Monocomponent fibers are generally formed from a polymer or blend of polymers extruded from a single extruder. Multicomponent fibers are generally formed from two or more polymers (e.g., bicomponent fibers) extruded from separate extruders. The polymers may be arranged in substantially constantly positioned distinct zones across the cross-section of the fibers. The components may be arranged in any desired configuration, such as sheath-core, side-by-side, pie, island-in-the-sea, three island, bull's eye, or various other arrangements known in the art. Multicomponent fibers having various irregular shapes may also be formed.

Fibers of any desired length may be employed, such as staple fibers, continuous fibers, etc. In one particular embodiment, for example, staple fibers may be used that have a fiber length in the range of from about 1 to about 150 millimeters, in some embodiments from about 5 to about 50 millimeters, in some embodiments from about 10 to about 40 millimeters, and in some embodiments, from about 10 to about 25 millimeters. Although not required, carding techniques may be employed to form fibrous layers with staple fibers as is well known in the art. For example, fibers may be formed into a carded web by placing bales of the fibers into a picker that separates the fibers. Next, the fibers are sent through a combing or carding unit that further breaks apart and aligns the fibers in the machine direction so as to form a machine direction-oriented fibrous nonwoven web. The carded web may then be bonded using known techniques to form a bonded carded nonwoven web.

If desired, the nonwoven web facing used to form the nonwoven composite may have a multi-layer structure. Suitable multi-layered materials may include, for instance, spunbond/meltblown/spunbond (SMS) laminates and spunbond/meltblown (SM) laminates. Another example of a multi-layered structure is a spunbond web produced on a multiple spin bank machine in which a spin bank deposits fibers over a layer of fibers deposited from a previous spin bank. Such an individual spunbond nonwoven web may also be thought of as a multi-layered structure. In this situation, the various layers of deposited fibers in the nonwoven web may be the same, or they may be different in basis weight and/or in terms of the composition, type, size, level of crimp, and/or shape of the fibers produced. As another example, a single nonwoven web may be provided as two or more individually produced layers of a spunbond web, a carded web, etc., which have been bonded together to form the nonwoven web. These individually produced layers may differ in terms of production method, basis weight, composition, and fibers as discussed above. A nonwoven web facing may also contain an additional fibrous component such that it is considered a composite. For example, a nonwoven web may be entangled with another fibrous component using any or a variety of entanglement techniques known in the art (e.g., hydraulic, air, mechanical, etc.). In one embodiment, the nonwoven web is integrally entangled with cellulosic fibers using hydraulic entanglement. A typical hydraulic entangling process utilizes high pressure jet streams of water to entangle fibers to form a highly entangled consolidated fibrous structure, e.g., a nonwoven web. The fibrous component of the composite may contain any desired amount of the resulting substrate.

Regardless of the particular manner in which it is formed, the film may be drawn to form the desired porous network. If desired, the film may be drawn in-line as it is being formed. Alternatively, the film may be drawn in its solid state after being formed, before and/or after lamination to any optional facing materials. By "solid state" drawing, it is generally meant that the composition is kept at a temperature below the melting temperature of the polyolefin matrix polymer. Among other things, this helps to ensure that the polymer chains are not altered to such an extent that the porous network becomes unstable. For example, the film may be drawn at a temperature of from about −50° C. to about 150° C., in some embodiments from about −40° C. to about 140° C., in some embodiments, from about −20° C. to about 100° C., and in some embodiments, from about 0° C. to about 50° C. In certain cases, the drawing temperature may optionally be at least about 10° C., in some embodiments at least about 20° C., and in some embodiments, at least about 30° C. below the glass transition temperature of the component having the highest glass transition temperature (e.g., microinclusion additive). In such embodiments the film may be drawn at a temperature of from about 0° C. to about 50° C., in some embodiments from about 15° C. to about 40° C., and in some embodiments, from about 20° C. to about 30° C.

Drawing may occur in one or multiple stages and using any of a variety of different techniques. In one embodiment, for example, the film may be drawn with a machine direction orienter ("MDO"), such as using the unit 100 shown in FIG. 1. To draw the film in the manner described above, it is typically desired that the rolls of the MDO are not heated. Nevertheless, if desired, one or more rolls may be heated to a slight extent to facilitate the drawing process so long as the temperature of the composition remains below the ranges noted above. The film is typically drawn (e.g., in the machine direction) to a draw ratio of from about 1.1 to about 3.5, in some embodiments from about 1.2 to about 3.0, and in some embodiments, from about 1.3 to about 2.5. The draw ratio may be determined by dividing the length of the drawn film by its length before drawing. The draw rate may also vary to help achieve the desired properties, such as within the range of from about 5% to about 1500% per minute of deformation, in some embodiments from about 20% to about 1000% per minute of deformation, and in some embodiments, from about 25% to about 850% per minute of deformation. Although the film is typically drawn without the application of external heat (e.g., heated rolls), such heat might be optionally employed to improve processability, reduce draw force, increase draw rates, and improve uniformity.

Drawing in the manner described above can result in the formation of pores that have a "nano-scale" cross-sectional dimension ("nanopores"), such as about 800 nanometers or less, in some embodiments from about 5 to about 700 nanometers, and in some embodiments, from about 10 to about 500 nanometers. The nanopores may also have an average axial dimension (e.g., length) of from about 100 to about 5000 nanometers, in some embodiments from about 50 to about 2000 nanometers, and in some embodiments, from about 100 to about 1000 nanometers. Micropores may also be formed during drawing that have an average cross-sectional dimension of about 0.2 micrometers or more, in some embodiments about 0.5 micrometers or more, and in some embodiments, from about 0.5 micrometers to about 5 micrometers. In certain cases, the axial dimension of the micropores and/or nanopores may be larger than the cross-sectional dimension so that the aspect ratio (the ratio of the axial dimension to the cross-sectional dimension) is from about 1 to about 30, in some embodiments from about 1.1 to about 15 and in some embodiments, from about 1.2 to about 5. For example, the axial dimension of the micropores may be 1 micrometer or more, in some embodiments about 1.5 micrometers or more, and in some embodiments, from about 2 to about 30 micrometers.

Regardless of their particular size, the present inventors have discovered that the pores (e.g., nanopores, micropores, or both) can be distributed in a substantially homogeneous fashion throughout the material. For example, the pores may be distributed in columns that are oriented in a direction generally perpendicular to the direction in which a stress is applied. These columns may be generally parallel to each other across the width of the material. Without intending to be limited by theory, it is believed that the presence of such a homogeneously distributed porous network can result in a high thermal resistance as well as good mechanical properties (e.g., energy dissipation under load and impact strength). This is in stark contrast to conventional techniques for creating pores that involve the use of blowing agents, which tend to result in an uncontrolled pore distribution and poor mechanical properties.

In addition to forming a porous network, drawing can also significantly increase the axial dimension of certain of the discrete domains so that they have a generally linear, elongated shape. For example, the elongated micro-scale domains may have an average axial dimension that is about 10% or more, in some embodiments from about 20% to about 500%, and in some embodiments, from about 50% to about 250% greater than the axial dimension of the domains prior to drawing. The axial dimension (e.g., length) after drawing may, for instance, range from about 1 µm to about 400 µm, in some embodiments from about 5 µm to about 200 µm, and in some embodiments from about 10 µm to about 150 µm. The micro-scale domains may also be relatively thin and thus have a small cross-sectional dimension, such as from about 0.02 to about 20 micrometers, in some embodiments from about 0.1 to about 10 micrometers, and in some embodiments, from 0.4 to about 5 micrometers. This may result in an aspect ratio for the domains (the ratio of the axial dimension to a dimension orthogonal to the axial dimension) of from about 2 to about 150, in some embodiments from about 3 to about 100, and in some embodiments, from about 4 to about 50. Due to their small size, the nano-scale domains are not typically elongated in the same manner as the micro-scale domains. Thus, the nano-scale domains may retain an average axial dimension (e.g., length) of from about 1 to about 1000 nanometers, in some embodiments from about 5 to about 800 nanometers, in some embodiments from about 10 to about 500 nanometers, and in some embodiments from about 20 to about 200 nanometers.

Even at the very low densities achieved by the present invention, the resulting film is not brittle and may be relatively ductile. One parameter that is indicative of good ductility is the peak elongation of the film in the machine direction ("MD") and/or cross-machine direction ("CD"). For example, the film typically exhibits a peak elongation in the machine direction of about 50% or more, in some embodiments about 60% or more, in some embodiments about 70% or more, and in some embodiments, from about 80% to about 200%. The film may likewise exhibit a peak elongation in the cross-machine direction of about 750% or more in some embodiments about 800% or more, in some embodiments about 800% or more, and in some embodiments, from about 850% to about 2500%. Despite having such good ductility, the film of the present invention is nevertheless able to retain good mechanical strength. For example, the film of the present invention may exhibit an ultimate tensile strength in the machine direction and/or cross-machine direction of from about 20 to about 150 Megapascals (MPa), in some embodiments from about 25 to about 120 MPa, and in some embodiment from about 30 to about 100 MPa. The Young's modulus of elasticity of the film, which is equal to the ratio of the tensile stress to the tensile strain and is determined from the slope of a stress-strain curve, may also be good. For example, the film typically exhibits a Young's modulus in the machine direction and/or cross-machine direction of from about 250 to about 10,00 MPa, in some embodiments from about 500 to about 8,000 MPa, and in some embodiments, from about 1,000 to about 5,000 MPa. Surprisingly, the good ductility and other mechanical properties can be achieved even though the film has a very low thickness. For example, the thickness of the film, after being drawn, may generally range from about 5 micrometers to about 1,000 micrometers, in some embodiments from about 10 to about 800 micrometers, and in some embodiments, from about 15 to about 600 micrometers. Of course the actual thickness may vary greatly depending on the intended type of packaging. For example, thin-gauge packaging films may have a thickness of from about 5 to about 100 micrometers, in some embodiments from about 10 to about 80 micrometers, and in some embodiments, from about 15 to about 40 micrometers. On the other hand, thick-gauge packaging films may range from about 100 to about 1,000 micrometers, in some embodiments from about 150 to about 800 micrometers, and in some embodiments, from about 200 to about 600 micrometers.

IV. Applications

Due to its unique properties, the film of the present invention is particularly suitable for use as a packaging film, such as an individual wrap, packaging pouches, bundle films, or bags for the use of a variety of articles, such as food products, paper products (e.g., tissue, wipes, paper towels, etc.), absorbent articles, etc. Various suitable pouch wrap, or bag configurations for absorbent articles are disclosed, for instance, in U.S. Pat. No. 6,716,203 to Sorebo, et al. and U.S. Pat. No. 6,380,445 to Moder, at al., as well as U.S. Patent Application Publication No. 2003/0116462 to Sorebo, et al.

The present invention may be better understood with reference to the following examples.

Test Methods

Melt Flow Rate:

The melt flow rate ("MFR") is the weight of a polymer (in grams) forced through an extrusion rheometer orifice (0.0825-inch diameter) when subjected to a load of 2160 grams in 10 minutes, typically at 190° C., 210° C., or 230° C. Unless otherwise indicated, melt flow rate is measured in accordance with ASTM Test Method D1238 with a Tinius Olsen Extrusion Plastometer.

Thermal Properties:

The glass transition temperature ($T_g$) may be determined by dynamic mechanical analysis (DMA) in accordance with ASTM E1640-09. A Q800 instrument from TA Instruments may be used. The experimental runs may be executed in tension/tension geometry, in a temperature sweep mode in the range from −120° C. to 150° C. with a heating rate of 3° C./min. The strain amplitude frequency may be kept constant (2 Hz) during the test. Three (3) independent samples may be tested to get an average glass transition temperature which is defined by the peak value of the tan δ curve, wherein tan δ is defined as the ratio of the loss modulus to the storage modulus (tan δ=E"/E').

The melting temperature may be determined by differential scanning calorimetry (DSC). The differential scanning calorimeter may be a DSC Q100 Differential Scanning Calorimeter, which was outfitted with a liquid nitrogen cooling accessory and with a UNIVERSAL ANALYSIS 2000 (version 4.6.6) analysis software program, both of which are available from T.A. Instruments Inc. of New Castle, Del. To avoid directly handling the samples, tweezers or other tools are used. The samples are placed into an aluminum pan and weighed to an accuracy of 0.01 milligram on an analytical balance. A lid is crimped over the material sample onto the pan. Typically, the resin pellets are placed directly in the weighing pan.

The differential scanning calorimeter is calibrated using an indium metal standard and a baseline correction is performed, as described in the operating manual for the differential scanning calorimeter. A material sample is placed into the test chamber of the differential scanning calorimeter for testing, and an empty pan is used as a reference. All testing is run with a 55-cubic centimeter per minute nitrogen (industrial grade) purge on the test chamber. For resin pellet samples, the heating and cooling program is a 2-cycle test that began with an equilibration of the chamber to −30° C., followed by a first heating period at a heating rate of 10° C. per minute to a temperature of 200° C., followed by equilibration of the sample at 200° C. for 3 minutes, followed by a first cooling period at a cooling rate of 10° C. per minute to a temperature of −30° C., followed by equilibration of the sample at −30° C. for 3 minutes, and then a second heating period at a heating rate of 10° C. per minute to a temperature of 200° C. All testing is run with a 55-cubic centimeter per minute nitrogen (industrial grade) purge on the test chamber.

The results are evaluated using the UNIVERSAL ANALYSIS 2000 analysis software program, which identified and quantified the glass transition temperature ($T_g$) of inflection, the endothermic and exothermic peaks, and the areas under the peaks on the DSC plots. The glass transition temperature is identified as the region on the plot-line where a distinct change in slope occurred, and the melting temperature is determined using an automatic inflection calculation.

Film Tensile Properties:

Films may be tested for tensile properties (peak stress, modulus, strain at break, and energy per volume at break) on a MTS Synergie 200 tensile frame. The test may be performed in accordance with ASTM D638-10 (at about 23° C.). Film samples may be cut into dog bone shapes with a center width of 3.0 mm before testing. The dog-bone film samples may be held in place using grips on the MIS Synergie 200 device with a gauge length of 18.0 mm. The film samples may be stretched at a crosshead speed of 5.0 in/min until breakage occurred. Five samples may be tested for each film in both the machine direction (MD) and the cross direction (CD). A computer program (e.g., TestWorks 4) may be used to collect data during testing and to generate a stress versus strain curve from which a number of properties may be determined, including modulus, peak, stress, elongation, and energy to break.

Density and Percent Void Volume:

To determine density and percent void volume, the width ($W_i$) and thickness ($T_i$) of the specimen may be initially measured prior to drawing. The length ($L_i$) before drawing may also be determined by measuring the distance between two markings on a surface of the specimen. Thereafter, the specimen may be drawn to initiate pore formation. The width ($W_f$), thickness ($T_f$), and length ($L_f$) of the specimen may then be measured to the nearest 0.01 mm utilizing Digimatic Caliper (Mitutoyo Corporation). The volume ($V_f$) before drawing may be calculated by $W_i \times T_i \times L_i = V_i$. The volume ($V_f$) after drawing may also be calculated by $W_f \times T_f \times L_f = V_f$. The density ($P_f$) may be calculated by $P_f = P_i/\Phi$, where $P_i$ is density of precursor material and the percent void volume (% $V_v$) was calculated by: % $V_v = (1 - 1/\Phi) \times 100$.

Hydrostatic Pressure Test ("Hydrohead"):

The hydrostatic pressure test is a measure of the resistance of a materiel to penetration by liquid water under a static pressure and is performed in accordance with AATCC Test Method 127-2008. The results for each specimen may be averaged and recorded in centimeters (cm). A higher value indicates greater resistance to water penetration.

Water Vapor Transmission Rate ("WVTR")

The test used to determine the WVTR of a material may vary based on the nature of the material. One technique for measuring the WVTR value is ASTM E96/96M-12, Procedure B. Another method involves the use of INDA Test Procedure IST-70.04 (01). The INDA test procedure is summarized as follows. A dry chamber is separated from a wet chamber of known temperature and humidity by a permanent guard film and the sample material to be tested. The purpose of the guard film is to define a definite air gap and to quiet or still the air in the air gap while the air gap is characterized. The dry chamber, guard film, and the wet chamber make up a diffusion cell in which the test film is sealed. The sample holder is known as the Permatran-W Model 100K manufactured by Mocon/Modern Controls, Inc., Minneapolis, Minn. A first test is made of the WVTR of the guard film and the air gap between an evaporator assembly that generates 100% relative humidity. Water vapor diffuses through the air gap and the guard film and then mixes with a dry gas flow that is proportional to water vapor concentration. The electrical signal is routed to a computer for processing. The computer calculates the transmission rate of the air gap and the guard film and stores the value for further use.

The transmission rate of the guard film and air gap is stored in the computer as CalC. The sample materiel then sealed in the test cell. Again, water vapor diffuses through the air gap to the guard film and the test material and then mixes with a dry gas flow that sweeps the test material. Also, again, this mixture is carried to the vapor sensor. The computer then calculates the transmission rate of the combination of the air gap, the guard film, and the test material. This information is then used to calculate the transmission rate at which moisture is transmitted through the test material according to the equation:

$$TR^{-1}_{test\ material} = TR^{-1}_{test\ material, guardfilm, airgap} - TR^{-1}_{guardfilm, airgap}$$

The were vapor transmission rate ("WVTR") then calculated as follows:

$$WVTR = \frac{F\rho_{sat(T)}RH}{AP_{sat(T)}(1-RH)}$$

wherein,

F=the flow of water vapor in $cm^3$ per minute;
$\rho_{sat(T)}$=the density of water in saturated air at temperature T;
RH=the relative humidity at specified locations in the cell;
A=the cross sectional area of the cell; and
$P_{sat(T)}$=the saturation vapor pressure of water vapor at temperature T.

Example 1

A blend of materials was formed that contained 91.5 wt. % polypropylene (Total Petrochemicals M-3661), 7.5 wt. % polylactic acid (Natureworks Ingeo 6251D), and 1.0 wt. % of a polyepoxide modifier (Arkema Lotader AX8900). This mixture was then melt blended via a twin screw extruder at 220° C. to form a homogeneous polymer blend. The molten polymer blend was extruded through a multi-filament die, quenched via water, and cut in to a pellet via underwater pelletizing system such as those available from Gala Industries of Eagle Rock, Va. The compounded pellet was then flood fed into a single screw extruder (24:1 length to diameter ratio) with a cast film die. Materials were melted at a temperature of 220° C. and extruded through a film die on to a casting roll at a temperature of 25° C. A melt draw force was applied to the molten film to reduce the thickness to approximately 177 to 203 micrometers.

Example 2

A film was formed as described in Example 1, except that the thickness was 254 to 279 micrometers.

Example 3

The film of Example 1 was solid state drawn in a tensile frame (e.g., Sintech 1/S frame available from MTS systems) at a rate of 50 millimeters per minute to a strain of 300%. After stretching, it was determined that the length of the film increased 5.2 times in the machine direction and the width of the film decreased by 20%.

Example 4

Figure 2:
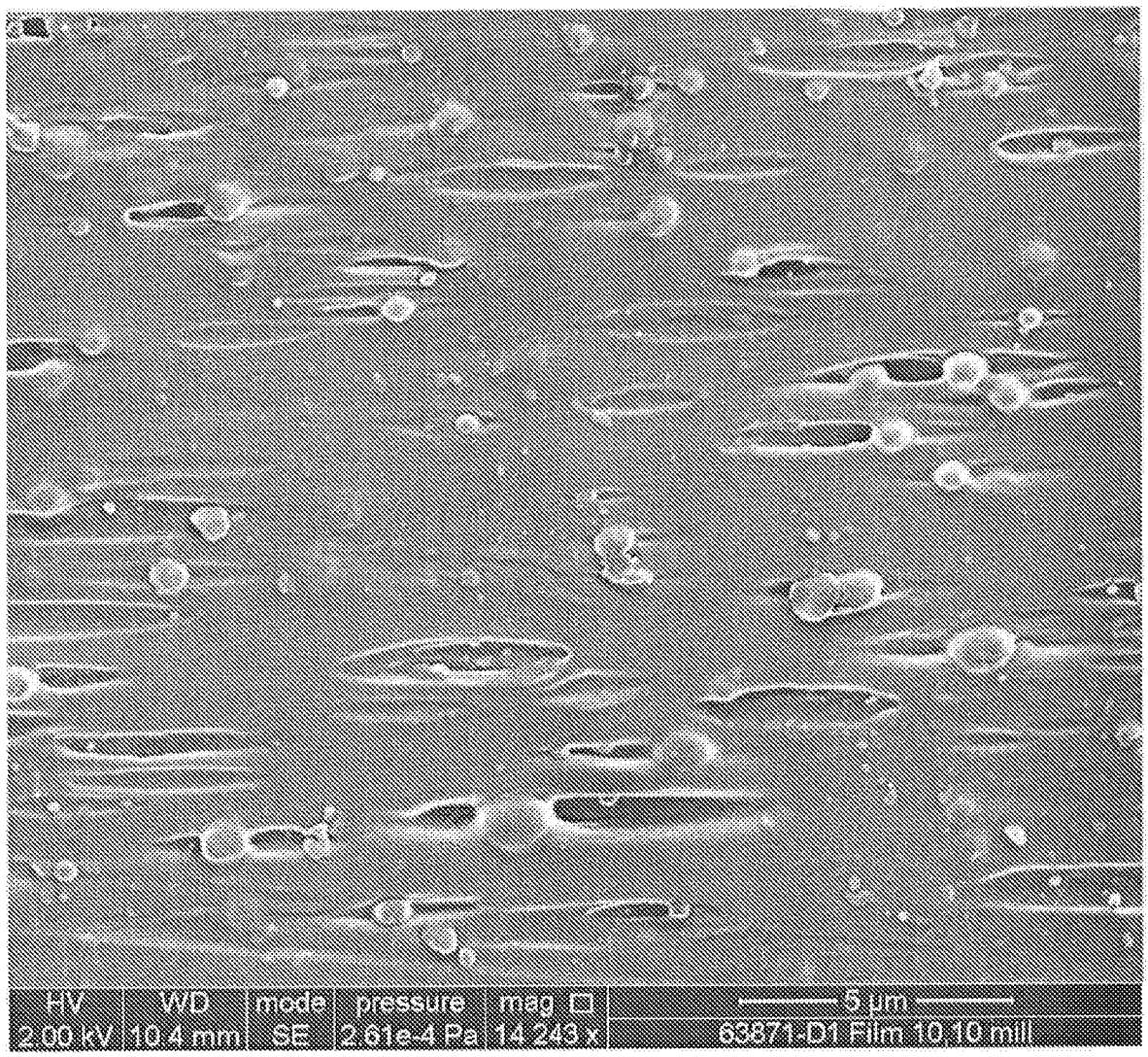
FIG. 2 is an SEM microphotograph of a surface of the film of Example 4 taken at a magnification of 14,243×.
Figure 3:
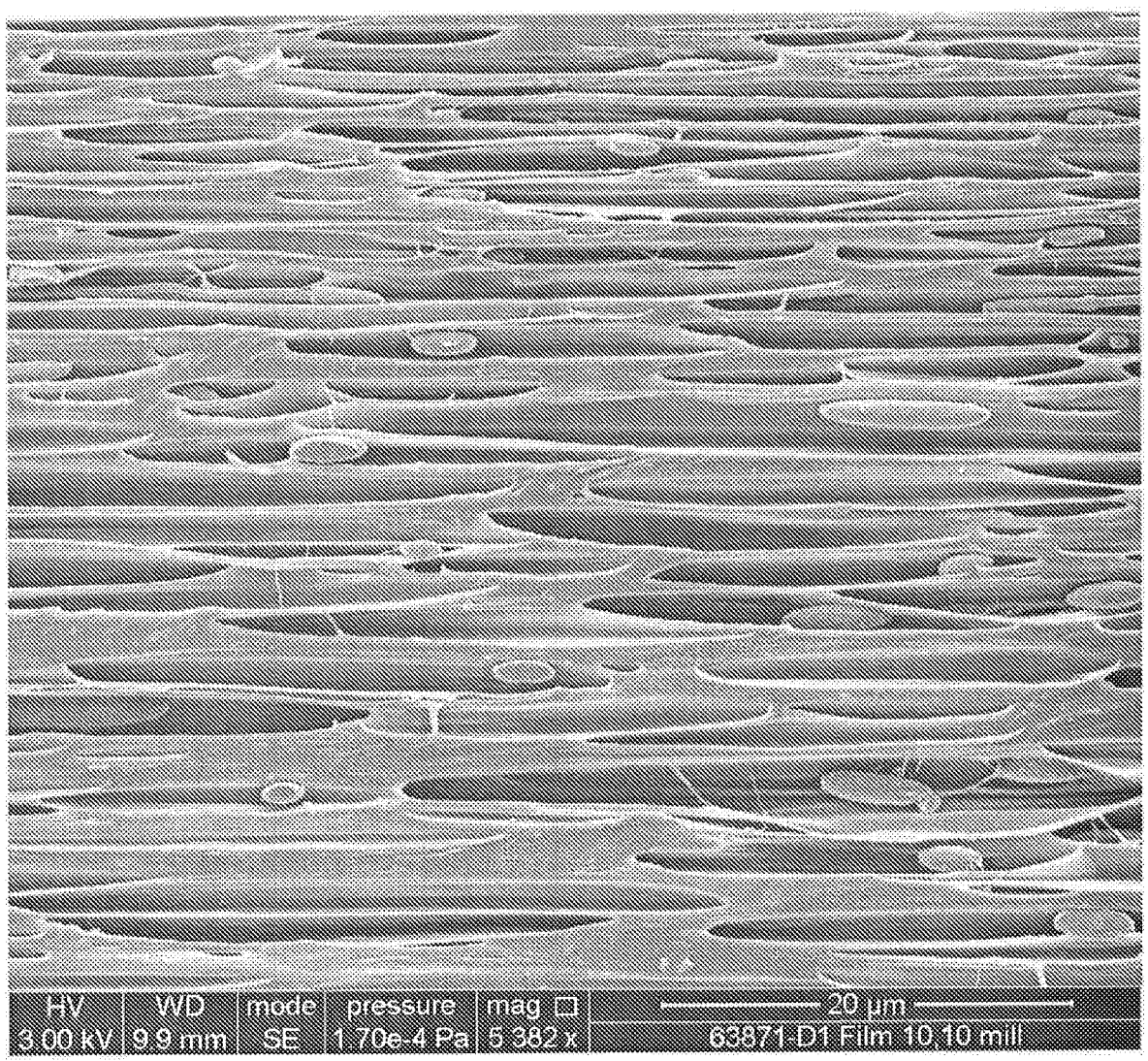
FIG. 3 is an SEM microphotograph of the film of Example 4 (cut in machine direction plane) taken at a magnification of 5,382×.

The film of Example 2 as solid state drawn in a tensile frame (e.g., Sintech 1/S frame available from MTS systems) at a rate of 50 millimeters per minute to a strain of 300%. After stretching, it was determined that the length of the film increased 5.6 times in the machine direction and the width of the film decreased by 20%. SEM microphotographs of the film are shown in FIGS. 2-3.

Various mechanical properties of the drawn films of Examples 3 and 4 were tested. The results are set forth in the table below.

|  | Thickness (μm) | Modulus (MPa) | Break Stress (MPa) | Strain at Break (%) |
| --- | --- | --- | --- | --- |
| Example 3 |  |  |  |  |
| MD | 64 | 3,480 | 156.9 | 19.2 |
| CD | 84 | 808 | 13.1 | 154.6 |

-continued

|  | Thickness (μm) | Modulus (MPa) | Break Stress (MPa) | Strain at Break (%) |
|---|---|---|---|---|
| Example 4 |  |  |  |  |
| MD | 84 | 3,452 | 160.3 | 15.9 |
| CD | 103 | 665 | 14.2 | 172.8 |

Example 5

A film was formed as described in Example 1, except that the thickness was 48 to 55 micrometers.

Example 6

A blend of materials was formed that contained 78 wt. % polypropylene (Total Petrochemicals M-3661), 15 wt. % polylactic acid (Natureworks Ingeo 6251D), and 7.0 wt. % of a polyepoxide modifier (Arkema Lotader AX8900). This mixture was then melt blended via a twin screw extruder at 220° C. to form a homogeneous polymer blend. The molten polymer blend was extruded through a multi-filament die, quenched via water, and cut in to a pellet via underwater pelletizing system such as those available from Gala Industries of Eagle Rock, Va. The compounded pellet was then flood fed into a single screw extruder (24:1 length to diameter ratio) with a cast film die. Materials were melted at a temperature of 220° C. and extruded through a film die on to a casting roll at a temperature of 25° C. A melt draw force was applied to the molten film to reduce the thickness to approximately 48 to 55 micrometers.

Example 7

A film was formed as described in Example 6, except that the thickness was 70 to 80 micrometers.

Example 8

A film was formed as described in Example 6, except that the thickness was 120 to 132 micrometers.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A drawn film comprising a thermoplastic composition, wherein the composition contains a continuous phase that includes a polyolefin matrix polymer and a polymeric nanoinclusion additive comprising a functionalized polyolefin and a polymeric microinclusion additive dispersed within the continuous phase in the form of discrete domains, wherein the polymeric nanoinclusion additive is in the form of nanoscale domains and the polymeric microinclusion additive is in the form of micro-scale domains,
wherein the continuous phase constitutes from about 60 wt. % to about 99 wt % of the thermoplastic composition,
wherein the nanoinclusion additive constitutes from about 0.01 wt. % to about 15 wt. % of the thermoplastic composition based on the weight of the thermoplastic composition,
wherein the microinclusion additive constitutes from about 0.1 wt. % to about 30 wt. % of the thermoplastic composition based on the weight of the thermoplastic composition,
wherein a porous network is defined in the composition that includes a plurality of nanopores adjacent to the nano-scale domains and/or the micro-scale domains and formed by drawing of the film, the nanopores having an average cross-sectional dimension of about 800 nanometers or less, and the total pore volume of the composition is from about 15% to about 80% per cubic centimeter, and
wherein the drawn film is a fluid-impermeable film having a hydrohead value of about 50 centimeters or more as determined in accordance with ATTCC 127-2008.

2. The film of claim 1, wherein the nanopores have an average cross-sectional dimension of from about 5 to about 700 nanometers.

3. The film of claim 1, wherein the nanopores have an average axial dimension of from about 100 to about 5000 nanometers.

4. The film of claim 1, wherein the polyolefin matrix polymer has a melt flow rate of from about 0.5 to about 80 grams per 10 minutes, determined at a load of 2160 grams and at 230° C. in accordance with ASTM D1238.

5. The film of claim 1, wherein the polyolefin matrix polymer is a propylene homopolymer, propylene/α-olefin copolymer, ethylene/α-olefin copolymer, or a combination thereof.

6. The film of claim 1, wherein the polyolefin matrix polymer is a substantially isotactic polypropylene homopolymer or a copolymer containing at least about 90% by weight propylene.

7. The film of claim 1, wherein the continuous phase constitutes from about 60 wt. % to about 98 wt. % of the thermoplastic composition.

8. The film of claim 1, wherein the functionalized polyolefin contains a polar component and a nonpolar component.

9. The film of claim 1, wherein the functionalized polyolefin is a polyepoxide.

10. The film of claim 1, wherein the nanoinclusion additive has melt flow rate of from about 0.1 to about 100 grams per 10 minutes, determined at a load of 2160 grams and at a temperature at least about 40° C. above the melting temperature in accordance with ASTM D1238.

11. The film of claim 10, wherein the ratio of the melt flow rate of the polyolefin matrix polymer to the melt flow rate of the nanoinclusion additive is from about 0.2 to about 8.

12. The film of claim 1, wherein the nano-scale domains have an average cross-sectional dimension of from about 1 nanometer to about 1000 nanometers.

13. The film of claim 1, wherein the nanoinclusion additive constitutes from about 0.1 wt. % to about 10 wt. % of the composition, based on the weight of the continuous phase.

14. The film of claim 1, wherein the microinclusion additive is a polymer that includes a styrenic copolymer, fluoropolymer, polyvinyl alcohol, polyvinyl acetate, or polyester.

15. The film of claim 1, wherein the polymer of the microinclusion additive is polylactic acid.

16. The film of claim 1, wherein the micro-scale domains have an average axial dimension of from about 1 micrometer to about 400 micrometers.

17. The film of claim 1, wherein the microinclusion additive constitutes from about 2 wt. % to about 25 wt. % of the composition, based on the weight of the continuous phase.

18. The film of claim 1, wherein the thermoplastic composition further comprises an interphase modifier.

19. The film of claim 1, wherein the porous network further includes micropores.

20. The film of claim 1, wherein the total pore volume of the composition is from about 20% to about 70% per cubic centimeter.

21. The film of claim 1, wherein nanopores constitute about 20 vol. % or more of the total pore volume of the composition.

22. The film of claim 1, wherein the thermoplastic composition has a density of about 0.90 $g/cm^3$ or less.

23. The film of claim 1, wherein the film has a water vapor transmission rate of about 300 $g/m^2/24$ hours or more.

24. The film of claim 1, wherein the film is a multi-layered film that contains a core layer and at least one outer layer, wherein the core layer, the outer layer, or both contain the thermoplastic composition.

25. The film of claim 1, wherein the polyolefin matrix polymer is an ethylene homopolymer, an ethylene/α-olefin copolymer, or a combination thereof.

26. The film of claim 1, wherein the microinclusion additive constitutes from about 0.5 wt. % to about 25 wt. % of the composition, based on the weight of the composition.

* * * * *